United States Patent
Rozen et al.

(10) Patent No.: US 7,319,145 B2
(45) Date of Patent: Jan. 15, 2008

(54) METHYLENETETRAHYDROFOLATE REDUCTASE INHIBITORS AND USE THEREOF

(75) Inventors: Rima Rozen, 9 Fairfield Crescent, Montreal West, Québec (CA) H4X 1R5; Jaspreet Sekhon, Vancouver (CA)

(73) Assignee: Rima Rozen, Montreal West, Quebec (CA)

( * ) Notice: Subject to any disclaimer, the term of this patent is extended or adjusted under 35 U.S.C. 154(b) by 0 days.

(21) Appl. No.: 10/433,392

(22) PCT Filed: Dec. 3, 2001

(86) PCT No.: PCT/CA01/01697

§ 371 (c)(1),
(2), (4) Date: Nov. 20, 2003

(87) PCT Pub. No.: WO02/43741

PCT Pub. Date: Jun. 6, 2002

(65) Prior Publication Data

US 2004/0121972 A1 Jun. 24, 2004

(51) Int. Cl.
C07H 21/04 (2006.01)
A61K 31/70 (2006.01)
C07H 21/00 (2006.01)
(52) U.S. Cl. .................... 536/24.5; 536/25.3; 514/44
(58) Field of Classification Search .................... 435/6; 514/44, 12; 424/146.1
See application file for complete search history.

(56) References Cited

U.S. PATENT DOCUMENTS

| 3,687,808 A | 8/1972 | Merigan, Jr. et al. |
| 5,512,438 A | 4/1996 | Ecker |
| 5,972,614 A | 10/1999 | Ruano et al. |
| 5,981,279 A * | 11/1999 | Weiss ........................ 435/375 |
| 5,998,206 A * | 12/1999 | Cowsert ..................... 435/375 |
| 6,008,221 A | 12/1999 | Smith et al. |
| 6,074,821 A | 6/2000 | Rozen et al. |
| 6,566,064 B1 * | 5/2003 | Shiraki et al. ................. 435/6 |
| 2002/0037507 A1 * | 3/2002 | WalkerPeach et al. ......... 435/6 |
| 2005/0101555 A1 * | 5/2005 | Zhang et al. ................. 514/44 |

FOREIGN PATENT DOCUMENTS

| GB | 9410620.0 | 5/1995 |
| WO | WO 88/04300 A1 | 6/1988 |
| WO | WO95/33054 | 12/1995 |
| WO | WO00/04194 | 1/2000 |
| WO | WO00/52205 | 9/2000 |
| WO | WO 00/52205 A3 | 9/2000 |

OTHER PUBLICATIONS

Branch TIBS 1998, vol. 23, p. 45-50.*
Opalinska et al. Nature Reviews Drug Discovery, 2002, vol. 1, p. 503-514.*
Matthews et al. Biochemistry, 1979, vol. 18, p. 4845-4851.*
Kutzbach et al. Biochimica et Biophysica Acta, 1967, vol. 139, p. 217-220.*
Alberts et al. (1983) Molecular Biology of The Cell, Garland Publishing Inc., New York, pp. 411-415.
Been and Cech (1986) Cell 47:207-216.
Bitko and Barik (2001) BMC Microbiol. 1:34.
Branch A. (1998) TIBS 23 pp. 45-50.
Bufalo et al., (1996) British J. Canc. 74:387-393.
Burton D. R. (1991) Proc. Natl. Acad. Sci. USA, 88:10134-10137.
Cech (1988) JAMA 260:3030.
Clarke et al. (1991) N. Engl. J. Med. 324:1149-1155.
Cole, S. P. et al. (1984) Mol. Cell Biol. 62:109-120.
Cote, R. J. et al. (1983) Proc. Natl. Acad. Sci. USA, 80:2026-2030.
Crooke et al. (1996) J. Pharmacol. Exp. Ther. 277:923-937.
Dean et al., (1996) Cancer Res. 56:3499-3507.
Elbashir et al. (2001) Nature 411:494-498.
Englisch et al. (1991) Angewandte Chemie, Int. Ed., 30:613.
Goding (1980) J. Imm. Meth. 39:285-308.
Hasegawa et al., (1998) Int. J. Cancer 76:812-816.
Haseloff and Gerlach (1988) Nature 334:585.
Huse, W. D. et al. (1989) Scienc,e 246:1275-1281.
Jefferies (1989) Nucleic Acids Research 17:1371.
Kabanov et al. (1990) FEBS Lett. 259:327-330.
Kim et al. (1987) Proc. Natl. Acad. Sci. USA 84:8788.
Kohler, G. et al. (1975) Nature 256:495-497.
Kozbor, D. et al. (1985) J. Immunol. Methods 81:31-42.
Krieg et al (1995) Nature 374:546-549.
Kutzbach et al. (1967) Biochim. Biophysica. Acta. 139:217-220.

(Continued)

Primary Examiner—Richard Schnizer
Assistant Examiner—Tracy Vivlemore
(74) Attorney, Agent, or Firm—Law Offices of Albert Wai-Kit Chan, PLLC

(57) ABSTRACT

The present invention provides methylenetetrahydrofolate reductase (MTHFR) inhibitors for use in selective inhibition of cancer cell growth in a mammal. These inhibitors can be a small molecule, an antisense oligonucleotide, a ribozyme, a triple helix forming oligonucleotide, an anti-MTHFR antibody or fragment thereof, an MTHFR mutant or a fragment of MTHFR. The present invention further provides nucleic acids encoding an inhibitor of MTHFR, and vectors comprising these nucleic acids. Also encompassed by the present invention are methods of using the MTHFR inhibitors for selective inhibition of cancer cell growth, and pharmaceutical compositions comprising the MTHFR inhibitors.

35 Claims, 17 Drawing Sheets

OTHER PUBLICATIONS

Letsinger et al (1989) Proc. Natl. Acad. Sci. USA 86:6553-6556.
Li et al. (1999) Clin. Cancer Res. 5:637-642.
Maddox, D. E. et al. (1983) J. Exp. Med. 158:1211-1216.
Manoharan et al. (1992) Ann. N.Y. Acad. Sci. 660:306-309.
Manoharan et al. (1994) Bioorg. Med. Chem. Let. 4:1053-1060.
Manoharan et al. (1993) Bioorg. Med. Chem. Lett. 3:2765-2770.
Manoharan et al. (1995) Nucleosides and Nucleotides 14:969-973.
Manoharan et al. (1995) Tetrahedron Lett. 36:3651-3654.
Martin et al. (1995) Helv. Chim. Acta. 78:486-504 Abstract only.
Matthews et al. (1979) Biochemistry 18(22):4845-4851.
Mishra et al. (1995) Biochim Biophysica Acta. 1264:229-237.
Morrison, S. L. et al. (1984) Proc. Natl. Acad. Sci. 81:6851-6855.
Narayanan, (1994) In Vivo 8: 787-794.
Needleman and Wunsch (1970) J. Mol. Biol. 48:443.
Neuberger, M. S. et al. (1984) Nature 312:604-608.
Nielsen et al. (1991) Science 254:1497-1500.
Oberhauser et al. (1992) Nucl. Acids Res. 20:533-538.
Opalinska et al. (2002) Nature Reviews Drug Discovery 1:503-514.
Orlandi, R. et al. (1989) Proc. Natl. Acad. Sci. 86: 3833-3837.
Pearson and Lipman (1988) Proc. Acad. Natl. Sci. (USA) 85:2444.
Saison-Behamoras et al. (1991) EMBO J. 10:1111-1118.
Sanghvi, Y.S. (1993) Antisense Research and Applications, pp. 289-302 and 276-278, Crooke, S.T. and Lebleu B., ed., CRC Press.
Sekhon et al. (2002) British Journal of Cancer 87:225-230.
Shea et al. (1990) Nucl. Acids. Res. 18:3777-3783.
Smith and Waterman (1981) Adv. Appl. Math. 2:482.
Svinarchuk et al. (1993) Biochimie 75:49-54.
Takeda, S. et al. (1985) Nature 314:452-454.
The Concise Encyclopedia Of Polymer Science and Engineering (1990) pp. 858-859, Kroschwitz, J.I. ed. John Wiley and Sons.
Winter, G. et al. (1991) Nature 349:293-299.
Zamore (2001) Nature Struct. Biol. 8:746-750.
Zaug and Cech (1986) Science 231:470-475.
Zaug et al. (1984) Science 224:574-578.
Zaug et al. (1986) Nature 324:429-433.
Bakker et al. Hyperhomocysteinaemia and associated disease. Pharm. World Sci. (1997) 19:126:132.
Brattstrom et al. Plasma Homocysteine and Methionine Tolerance in Early-Onset Vascular Disease. Haemostasis (1989) 19:35-44.
Chen et al. A Methylenetetrahydrofolate Reductase Polymorphism and the Risk of Colorectal Cancer. Cancer Research (1996) 56:4862-4864.
Chen et al. MTHFR Polymorphism, Methyl-Replete Diets and the Risk of Colorectal Carcinoma and Adenoma among U.S. Men and Women: An Example of Gene-Environment Interactions in Colorectal Tumorigenesis. American Society for Nutritional Sciences (1996) p. 560S-564S.
Engbersen et al. Thermolabile 5,10-Methylenetetrahydrofolate Reductase as a Cause of Mild Hyperhomocysteinemia. Am. J. Hum. Genet. (1995) 56:142-150.
Goyette et al. Seven Novel Mutations in the Methylenetetrahydrofolate Reductase Gene and Genotype/Phenotype Correlations in Severe Methylenetetrahydrofolate Reductase Deficiency. Am. J. Hum. Genet. (1995) 56: 1052-1059.
Goyette et al. Severe Mild Mutations in cis for the Methlenetetrahydrofolate Reductase (MTHFR) Gene, and Description of Five Novel Mutations in MTHFR. Am. J. Hum. Genet. (1996) 59:1268-1275.
Grandone et al. Factor V Leiden, C>T MTHFR Polymorphism and Genetic Susceptibility to Preeclampsia. Thromb. Haemost (1997) 77:1052-1054.
Greico. Homocystinuria: pathogenetic mechanisms. Am. J. of Med. Sci. (1977) 273:120-132.
Third Wave Technologies Launches Third Pharmacogenetic Product: Oligonucleotide Sets and Assay Controls Specific for MTHFR Mutation (Madison, WI—Dec. 9, 1999)—News Release—Third Wave Technologies.
van der Put et al. A Second Common Mutation in the Methylenetetrahydrofolate Reductase Gene: An Additional Risk Factor for Neural-Tube Defects? Am. J. Hum. Genet. (1998) 62:1044-1051.
Rozen, R. Molecular Genetics of Methylenetetrahydrofolate Reductase Deficiency, J. Inher Metab. Dis. (1996) 16:589-594.
Agrawal et al., "Antisense Therapeutics: Is it as simple as complementary base recognition?" Molecular Medicine Today 6, 72-81 (2000).
Bennett, F.C. et al., Pharmacology of Antisense Therapeutic Agents: Methods in Molecular Medicine: Antisense Therapeutics, 13-46 (1996).
Flanagan W.M. et al ., "Cellular Penetration and Antisense Activity by a Phenioxazine -Substituted Heptancleotide" Research , 1-5 (1998).
Green D.W. et al., "Antisense Oligonucleotides: An evolving Technology for the Modulation of Gene Expression in Human Disease." American College of Surgeons, 1, 93-103 (2000).
Jen K-Y et al., Suppression of Gene Expression by targeted disruption of messanger RNA: Available Options and Current Strategies, 18, 307-319 (2000).
Ma et al., "Synthetic Oligonucleotides as Therapeutices: The Coming of Age." Biotechnology Annual Review 5, 155-196 (2000).
Agrawal et al., 1999. *Biochimica et Biophysica Acta* 1489:53-68.
Akar et al., 2000. *Throm. Res.* 97:163-167.
Araki et al., 1987. J. Chromatography 422:43-52.
Arlnami et al., 1997. Amer. J. of Medical Genetics 74:526-528.
Boushey et al., 1995. JAMA 274:1049-1057.
Chapman et al. 1998. Stroke. 29:1401-1404.
Chen et al., 1998. Carcinogenesis 19(12):2129-2132.
Christensen et al., 1997. Arteriosclerosis, Thrombosis, and Vascular Biology 17:569-573.
Esteller et al., 1997. Carcinogenesis 18(12): 2307-2311.
Fletcher et al., 1998. Human Genet. 103:11-21.
Freeman et al., 1975. N.E. Journal of Medicine 292:491-496.
Frosst et al., 1995. Nature Genetics 10:111-113.
Gallagher et al., 1996. Circulation 94:2154-2158.
Gaughan et al., 2000. Gene 257:279-289.
Goyette et al., 1998 Mammalian Genome 9:652-656.
Goyette et al., 1994. Nature Genetics 7:195-200.
Grandone et al., 1998. Thrombosis. And .Haemostasis 79:1056-1057.
Gudnason et al., "C677T (thermolabile alanine/valine) polymorphism in methylenetetrahydrofolate reductase (MTHFR): its frequency and impact on plasma homocysteine concentration in different European populations." Atherosclerosis 136:347-354 (1998).
Haagsma et al., "Influence of sulphasalazine, methotrexate, and the combination of both on plasma homocysteine concentrations in patients with rheumatoid arthritis," Ann. Rheum. Dis. 58:79-84 (1999).
Haworth et al., "Symptomatic and asymptomatic methylenetetrahydrofolate reductase deficiency in two adult brothers." Am. J. of Medical Genetics 45:572-576 (1993).
Hol et al., "molecular genetic analysis of the gene encoding the trifunctional enzyme MTHFR(methylenehydrofolate-cyclohydrolase, formyltetrahydrofolate synthetase) in patients with neural tube defects," Clin. Genet. 53:119-125 (1998).
Homberger et al., "Genomic structure and transcript variants of the human methylenetetrahydrofolate reductase gene," Eur. J. Hum. Genet. 8:725-729 (2000).
Jacques et al., "Relation Between Folate Status, A Common Mutation in Methylenetetrahydrofolate Reductase, and Plasma Homocysteine Concentrations," Circulation 93:7-9 (1996).
James et al., "Abnormal folate metabolism and mutation in the methylenetetrahydrofolate reductase gene may be maternal risk factors for Down syndrome," Am. J. Clin. Nutr. 70:495-501, 1999.
Kang et al., "Thermolabile methylenetetrahydrofolate reductase: An inherited risk factor for coronary artery disease," Am. J. Human Genet. 48:536-545 (1991).
Kluljtmans et al. "Molecular genetic analysis in mild hyperhomocysteinemia: A common mutation in methylenetetrahydrofolate reductase gene is a risk factor for cardiovascular disease," Am. J. Hum. Genet. 58:35-41 (1996).
Kohn et al., Potential Applications of Gene Therapy, Transfusion 29(9):812-820, (1989).

Kunugi et al., "C677T polymorphism in methylenetetrahydrofolate reductase gene and psychoses," Mol. Psychiatr. 3:435-437 (1998).

Lanoue et al., "Antisense Inhibition of Methylenetetrahydrofolate Reductase Results in Neural Tube Defects in Cultured Mouse Embryos," Experimental Biology Abstract (1997).

Marugame et al., "Methylenetetrahydrofolate Reductase polymorphism and risk of colorectal adenomas," Cancer Letters 151:181-186 (2000).

Matthews et al. "Methylenetetrahydrofolate reductase and methionine synthase: biochemistry and molecular biology," Eur. J. Pediatr. 157: S54-S59 (1998).

Matthews, Methylenetetrahydrofolate reductase from pig liver, Methods in Enzymology Vitamines and Coenzymes Part G 122:372-381 (1986).

Morita et al., "Genetic polymorphism of 5, 10 methylenetetrahydrofolate reductase (MTHFR) as a risk factor for coronary artery disease," Circulation 95:2032-2036 (1997).

Mudd et al., "$N^{5,10}$-methylenetetrahydrofolate reductase deficiency and schizophrenia: a working hypothesis," J. Psychiat. Res. 11:259-262 (1974).

Neckers et al., Methods of Molecular Medicine: Antisense Therapeutics, Agrawal, Ed., Humana Press, Totawa, New Jersey (1996).

Orita et al., "Rapid and Sensitive Detection of Point Mutations and DNA Polymorphisms Using the Polymerase Chain Reaction," Genomics 5:874-879 (1989).

Park et al., "The 677C>T mutation in 5,10-methylenetetrahydrofolate reductase and colorectal cancer risk," Genetic Testing 3(2):233-236 (1999).

Pasquier et al., "Methylenetetrahydrofolate reductase deficiency revealed by a neuropathy in a psychotic adult [letter]," Journal of Neurology, Neurosurgery & Psychiatry 57:765-766 (1994).

Patzel et al., "A theoretical approach to select effective antisense oligodeoxyribonucleotides at high statistical probability," Nucleic Acid Research 27:4328-4334 (1999).

Pereira, "Evaluation of methylenetetrahydrofolate reductase for targeted therapeutics in cancer," McGill University, Dec. 1999.

Refsum et al., "Homocysteine and vascular disease," Annu. Rev. Medicine 48:31-62 (1998).

Regland et al., "Homozygous thermolabile methylenetetrahydrofolate reductase in schizophrenia-like psychosis," Journal of Neural transmission 104:931-941 (1997).

Rozen et al., "Molecular genetics of methylenetetrahydrofolate reductase deficiency," J. Inher. Metab. Dis. 19:589-594 (1996).

Rozen et al., U.S. Appl. No. 09/592,595, filed Jun. 12, 2000.

Rozen et al., U.S. Appl. No. 09/258,928, filed Mar. 1, 1999.

Saint-Girons et al., "Nucleotide sequence of metF, the *E. coli* structural gene for 5-10 methylenetetrahydrofolate reductase and of its control region," Nucleic Acids Research 11:6723-6732.

Schwartz et al., "Myocardial Infarction in young Women In Relation To Plasma Total Homocysteine, Folate, And A Common Variant In The Methylenetetrahydrofolate Reductase Gene," Circulation 96(2): 412-417 (1997).

Skibola et al., "Polymorphisms in the methylenetetrahydrofolate reductase gene are associated with susceptibility to acute leukemia in adults," Proc. Natl. Acad. Sci. USA 96:12810-12815 (1999).

Slattery et al., "Methylenetetrahydrofolate reductase, diet, and risk of colon cancer," Cancer Epidemiology, Biomarkers & Prevention 8:513-518 (1999).

Sohda et al., "methylenetetrahydrofolate reductase polymorphism and pre-eclampsia," J. Med. Genet. 34:525-526 (1997).

Stauffer et al., "Cloning and nucleotide sequence of the *Salmonella typhimurium* LT2 metF gene and its homology with the corresponding sequence of *Escherichia coli*," Mol. Gen. Genet. 212:246-251 (1998).

Third Wave Technologies, "Third Wave Technologies Launches Third Pharmacogenetic Product Oligonucleotide Sets and Assay Controls Specific for MTHFR Mutation," News release Dec. 1999.

Ulrich et al., "Colorectal adenomas and the C677T MTHFR polymorphism: evidence for gene-environment interaction?" Cancer Epidemiology, Biomarkers & Prevention 8:659-668 (1999). Van der Put et al., "A second common Mutation in the methylenetetrahydrofolate reductase Gene: An Additional Risk Factor for Neural-Tube Defects?," Amer. J. Hum. Genet. 62:1044-1051 (1998).

Van der Put et al., "Mutated methylenetetrahydrofolate reductase as a risk factor for spina bifida," Lancet 346:1070-1071 (1995).

Van Ede et al., "Methotrezate in Rheumatoid Arthritis: An Update With Focus on Mechanisms Involved in Toxicity," Seminars in Arthritis and Rheumatism 27:277-292 (1998).

Viel et al., "Loss of heterozygosity at the 5, 10-methylenetetrahydrofolate reductase locus in human ovarian carcinomas," British Journal of Cancer 75:1105-1110 (1997).

Weisberg et al., "A second genetic polymorphism in methylenetetrahydrofolate reductase (MTHFR) Associated with decreased enzyme activity," Molecular Genetics and Metabolism 64:169-172 (1998).

Whitehead et al., "A genetic defect in 5, 10 methylenetetrahydrofolate reductase in neural tube defects," Q. J. Med. 88:763-766 (1995).

Wisotzkey et al., "MTHFR (C677T) polymorphisms and stage III colon cancer: response to therapy," Molecular Diagnosis 4(2):95-99 (1999).

Yacyshyn et al., "A placebo-controlled trial of ICAM-1 antisense oligonucleotide in the treatment of Crohn's disease," Gastroenterology 114: 1133-1142 (1998).

Zhou et al., "Purification and Characterization of methylenetetrahydrofolate reductase from Human Cadaver Liver," Biochemical Medicine and Metabolic Biology 43:234-242 (1990).

\* cited by examiner

```
AAT TCC GGA GCC ATG GTG AAC GAA GCC AGA GGA AAC AGC AGC CTC AAC CCC TGC TTG GAG   60
            Met Val Asn Glu Ala Arg Gly Asn Ser Ser Leu Asn Pro Cys Leu Glu    18

GGC AGT GCC AGC AGT GGC AGT GAG AGC TCC AAA GAT AGT TCG AGA TGT TCC ACC CCG GGC  120
Gly Ser Ala Ser Ser Gly Ser Glu Ser Ser Lys Asp Ser Ser Arg Cys Ser Thr Pro Gly   36

CTG GAC CCT GAG CGG CAT GAG AGA CTC CGG GAG AAG ATG AGG CGG CGA TTG GAA TCT GGT  180
Leu Asp Pro Glu Arg His Glu Arg Leu Arg Glu Lys Met Arg Arg Arg Leu Glu Ser Gly   56

GAC AAG TGG TTC TCC CTG GAA TTC TTC CCT CCT CGA ACT GCT GAG GGA GCT GTC AAT CTC  240
Asp Lys Trp Phe Ser Leu Glu Phe Phe Pro Pro Arg Thr Ala Glu Gly Ala Val Asn Leu   76

ATC TCA AGG TTT GAC CGG ATG GCA GCA GGT GGC CCC CTC TAC ATA GAC GTG ACC TGG CAC  300
Ile Ser Arg Phe Asp Arg Met Ala Ala Gly Gly Pro Leu Tyr Ile Asp Val Thr Trp His   96

CCA GCA GGT GAC CCT GGC TCA GAC AAG GAG ACC TCC TCC ATG ATG ATC GCC AGC ACT GCC  360
Pro Ala Gly Asp Pro Gly Ser Asp Lys Glu Thr Ser Ser Met Met Ile Ala Ser Thr Ala  116

GTG AAC TAC TGT GGC CTG GAG ACC ATC CTG CAC ATG ACC TGC TGC CGT CAG CGC CTG GAG  420
Val Asn Tyr Cys Gly Leu Glu Thr Ile Leu His Met Thr Cys Cys Arg Gln Arg Leu Glu  136

GAG ATC ACG GGC CAT CTG CAC AAA GCT AAG CAG CTG GGC CTG AAG AAC ATC ATG GCG CTG  480
Glu Ile Thr Gly His Leu His Lys Ala Lys Gln Leu Gly Leu Lys Asn Ile Met Ala Leu  156

CGG GGA GAC CCA ATA GGT GAC CAG TGG GAA GAG GAG GAG GGA GGC TTC AAC TAC GCA GTG  540
Arg Gly Asp Pro Ile Gly Asp Gln Trp Glu Glu Glu Glu Gly Gly Phe Asn Tyr Ala Val  176

GAC CTG GTG AAG CAC ATC CGA AGT GAG TTT GGT GAC TAC TTT GAC ATC TGT GTG GCA GGT  600
Asp Leu Val Lys His Ile Arg Ser Glu Phe Gly Asp Tyr Phe Asp Ile Cys Val Ala Gly  196

TAC CCC AAA GGC CAC CCC GAA GCA GGG AGC TTT GAG GCT GAC CTG AAG CAC TTG AAG GAG  660
Tyr Pro Lys Gly His Pro Glu Ala Gly Ser Phe Glu Ala Asp Leu Lys His Leu Lys Glu  216

AAG GTG TCT GCG GGA GCC GAT TTC ATC ATC ACG CAG CTT TTC TTT GAG GCT GAC ACA TTC  720
Lys Val Ser Ala Gly Ala Asp Phe Ile Ile Thr Gln Leu Phe Phe Glu Ala Asp Thr Phe  236
```

Figure 1A

```
TTC CGC TTT GTG AAG GCA TGC ACC GAC ATG GGC ATC ACT TGC CCC ATC GTC CCC GGG ATC  768
Phe Arg Phe Val Lys Ala Cys Thr Asp Met Gly Ile Thr Cys Pro Ile Val Pro Gly Ile  256

TTT CCC ATC CAG GGC TAC CAC TCC CTT CGG CAG CTT GTG AAG CTG TCC AAG CTG GAG GTG  828
Phe Pro Ile Gln Gly Tyr His Ser Leu Arg Gln Leu Val Lys Leu Ser Lys Leu Glu Val  276

CCA CAG GAG ATC AAG GAC GTG ATT GAG CCA ATC AAA GAC AAC GAT GCT GCC ATC CGC AAC  888
Pro Gln Glu Ile Lys Asp Val Ile Glu Pro Ile Lys Asp Asn Asp Ala Ala Ile Arg Asn  296

TAT GGC ATC GAG CTG GCC GTG AGC CTG TGC CAG GAG CTT CTG GCC AGT GGC TTG GTG CCA  948
Tyr Gly Ile Glu Leu Ala Val Ser Leu Cys Gln Glu Leu Leu Ala Ser Gly Leu Val Pro  316

GGC CTC CAC TTC TAC ACC CTC AAC CGC GAG ATG GCT ACC ACA GAG GTG CTG AAG CGC CTG 1008
Gly Leu His Phe Tyr Thr Leu Asn Arg Glu Met Ala Thr Thr Glu Val Leu Lys Arg Leu  336

GGG ATG TGG ACT GAG GAC CCC AGG CGT CCC CTA CCC TGG GCT CTC AGT GCC CAC CCC AAG 1068
Gly Met Trp Thr Glu Asp Pro Arg Arg Pro Leu Pro Trp Ala Leu Ser Ala His Pro Lys  356

CGC CGA GAG GAA GAT GTA CGT CCC ATC TTC TGG GCC TCC AGA CCA AAG AGT TAC ATC TAC 1128
Arg Arg Glu Glu Asp Val Arg Pro Ile Phe Trp Ala Ser Arg Pro Lys Ser Tyr Ile Tyr  376

CGT ACC CAG GAG TGG GAC GAG TTC CCT AAC GGC CGC TGG GGC AAT TCC TCT TCC CCT GCC 1188
Arg Thr Gln Glu Trp Asp Glu Phe Pro Asn Gly Arg Trp Gly Asn Ser Ser Ser Pro Ala  396

TTT GGG GAG CTG AAG GAC TAC TAC CTC TTC TAC CTG AAG AGC AAG TCC CCC AAG GAG GAG 1248
Phe Gly Glu Leu Lys Asp Tyr Tyr Leu Phe Tyr Leu Lys Ser Lys Ser Pro Lys Glu Glu  416

CTG CTG AAG ATG TGG GGG GAG GAG CTG ACC AGT GAA GCA AGT GTC TTT GAA GTC TTT GTT 1308
Leu Leu Lys Met Trp Gly Glu Glu Leu Thr Ser Glu Ala Ser Val Phe Glu Val Phe Val  436

CTT TAC CTC TCG GGA GAA CCA AAC CGG AAT GGT CAC AAA GTG ACT TGC CTG CCC TGG AAC 1368
Leu Tyr Leu Ser Gly Glu Pro Asn Arg Asn Gly His Lys Val Thr Cys Leu Pro Trp Asn  456

GAT GAG CCC CTG GCG GCT GAG ACC AGC CTG CTG AAG GAG GAG CTG CTG CGG GTG AAC CGC 1428
Asp Glu Pro Leu Ala Ala Glu Thr Ser Leu Leu Lys Glu Glu Leu Leu Arg Val Asn Arg  476
```

Figure 1B

```
CAG GGC ATC CTC ACC ATC AAC TCA CAG CCC AAC ATC AAC GGG AAG CCG TCC TCC GAC CCC  1500
Gln Gly Ile Leu Thr Ile Asn Ser Gln Pro Asn Ile Asn Gly Lys Pro Ser Ser Asp Pro   496

ATC GTG GGC TGG GGC CCC AGC GGG GGC TAT GTC TTC CAG AAG GCC TAC TTA GAG TTT TTC  1560
Ile Val Gly Trp Gly Pro Ser Gly Gly Tyr Val Phe Gln Lys Ala Tyr Leu Glu Phe Phe   516

ACT TCC CGC GAG ACA GCG GAA GCA CTT CTG CAA GTG CTG AAG AAG TAC GAG CTC CGG GTT  1620
Thr Ser Arg Glu Thr Ala Glu Ala Leu Leu Gln Val Leu Lys Lys Tyr Glu Leu Arg Val   536

AAT TAC CAC CTT GTC AAT GTG AAG GGT GAA AAC ATC ACC AAT GCC CCT GAA CTG CAG CCG  1680
Asn Tyr His Leu Val Asn Val Lys Gly Glu Asn Ile Thr Asn Ala Pro Glu Leu Gln Pro   556

AAT GCT GTC ACT TGG GGC ATC TTC CCT GGG CGA GAG ATC ATC CAG CCC ACC GTA GTG GAT  1740
Asn Ala Val Thr Trp Gly Ile Phe Pro Gly Arg Glu Ile Ile Gln Pro Thr Val Val Asp   576

CCC GTC AGC TTC ATG TTC TGG AAG GAC GAG GCC TTT GCC CTG TGG ATT GAG CGG TGG GGA  1800
Pro Val Ser Phe Met Phe Trp Lys Asp Glu Ala Phe Ala Leu Trp Ile Glu Arg Trp Gly   596

AAG CTG TAT GAG GAG GAG TCC CCG TCC CGC ACC ATC ATC CAG TAC ATC CAC GAC AAC TAC  1860
Lys Leu Tyr Glu Glu Glu Ser Pro Ser Arg Thr Ile Ile Gln Tyr Ile His Asp Asn Tyr   616

TTC CAG GTC AAC CTG GTG GAC AAT GAC TTC CCA CTG GAC AAC TGC CTC TGG CAG GTG GTG  1920
Phe Gln Val Asn Leu Val Asp Asn Asp Phe Pro Leu Asp Asn Cys Leu Trp Gln Val Val   636

GAA GAC ACA TTG GAG CTT CTC AAC AGG CCC ACC CAG AAT GCG AGA GAA ACG GAG GCT CCA  1980
Glu Asp Thr Leu Glu Leu Leu Asn Arg Pro Thr Gln Asn Ala Arg Glu Thr Glu Ala Pro   656

TGA CCC TGC GTC CTG ACG CCC TGC GTT GGA GCC ACT CCT GTC CTG CCT TCC TCC TCC ACA  2040
End

GTG CTG CTT CTC TTG GGA ACT CCA CTC TCC TTC GTG TCT CTC CCA CCC CGG CCT CCA CTC  2100

CCC CAC CTG ACA ATG GCA GCT AGA CTG GAG TGA GGC TTC CAG GCT CTT CCT GGA CCT GAG  2160

TCG GCC CCA CAT GGG AAC CTA GTA CTC TCT GCT CTA AAA AAA AAA AAA AAG GAA TT      2220
```

Figure 1C

EXON 1: 246 bp          (bp 3-248)

```
         gggtgtggct gcctgccccc tgatgctccc tgccccaccc tgtgcagtag GAACCCAGCC
ATGGTGAACG AAGCCAGAGG AAACAGCAGC CTCAACCCCT GCTTGGAGGG CAGTGCCAGC
AGTGGCAGTG AGAGCTCCAA AGATAGTTCG AGATGTTCCA CCCCGGGCCT GGACCCTGAG
CGGCATGAGA GACTCCGGGA GAAGATGAGG CGGCGATTGG AATCTGGTGA CAAGTGGTTC
TCCCTGGAAT TCTTCCCTCC TCGAACTGCT GAGGGAGCTG TCAATCTCAT CTCAAGgtaa
actcatgcaa ggttaaggtg agaggcggga gtggtggtgc ctgggg
```

EXON 2: 239 bp          (bp 249-487)

```
         acggatgg tatttctcct ggaacctctc ttcagaaaca aaccccctacag GTTTGACCGG
ATGGCAGCAG GTGGCCCCCT CTACATAGAC GTGACCTGGC ACCCAGCAGG TGACCCTGGC
TCAGACAAGG AGACCTCCTC CATGATGATC GCCAGCACCG CCGTGAACTA CTGTGGCCTG
GAGACCATCC TGCACATGAC CTGCTGCCGT CAGCGCCTGG AGGAGATCAC GGGCCATCTG
CACAAAGCTA AGCAGCTGGG CCTGAAGAAC ATCATGGCGC TGCGGGAGg tgtggagcca
gcactcccct acactctggg ttctggcttt cccggaggc
```

EXON 3: 111 bp          (bp 488-598)

```
tctggaggtt gggtgagacc cagtgactat gacctccacc aaccctgcag ACCCAATAGG
TGACCAGTGG GAAGAGGAGG AGGGAGGCTT CAACTACGCA GTGGACCTGG TGAAGCACAT
CCGAAGTGAG TTTGGTGACT ACTTTGACAT CTGTGTGGCA Ggtgagtggc tggatcatcc
tggtggcggg gatggagcta gggaggctga
```

EXON 4: 194 bp          (bp 599-792)
```
ccttgaacag gtggaggcca gcctctcctg actgtcatcc ctattggcag GTTACGCCAA
AGGCCACCCC GAAGCAGGGA GCTTTGAGGC TGACCTGAAG CACTTGAAGG AGAAGGTCTC
TGCGGGAGCC GATTTCATCA TCACGCAGCT TTTCTTTGAG GCTGACACAT TCTTCCGCTT
TGTGAAGGCA TGCACCGACA TGGGCATCAC TTGCCCCATC GTCCCCGGGA TCTTTCCCAT
CCAGgtgagg ggcccaggag agcccataag ctccctccac cccactctca ccgc
```

EXON 5: 251 bp          (bp 793-1043)

```
gctggccagc agccgccaca gccctcatg tcttggacag GGCTACCACT CCCTTCGGCA
GCTTGTGAAG CTGTCCAAGC TGGAGGTGCC ACAGGAGATC AAGGACGTGA TTGAGCCAAT
CAAAGACAAC GATGCTGCCA TCCGCAACTA TGGCATCGAG CTGGCCGTGA GCCTGTGCCA
GGAGCTTCTG GCCAGTGGCT TGTGCCAGG CCTCCACTTC TACACCCTCA ACCGCGAGAT
GGCTACCACA GAGGTGCTGA AGCGCCTGGG GATGTGGACT GAGGACCCCA Ggtgagggca
gtggcccaga gatccccaga ggagggtcca agagcagccc c
```

EXON 6: 135 bp          (bp 1044-1178)

```
tccctctagc caatccttg tctcaattct ctgtccccat cctcacccag GCGTCCCCTA
CCCTGGGCTC TCAGTGCCCA CCCCAAGCGC CGAGAGGAAG ATGTACGTCC CATCTTCTGG
GCCTCCAGAC CAAAGAGTTA CATCTACCGT ACCCAGGAGT GGGACGAGTT CCCTAACGGC
CGCTGgtgag ggcctgcaga ccttccttgc aaatacatct ttgttcttgg gagcg
```

Figure 2A

EXON 7: 181 bp        (bp 1179-1359)

```
    actgccctct gtcaggagtg tgccctgacc tctgggcacc cctctgccag GGGCAATTCC
    TCTTCCCCTG CCTTTGGGGA GCTGAAGGAC TACTACCTCT TCTACCTGAA GAGCAAGTCC
    CCCAAGGAGG AGCTGCTGAA GATGTGGGGG GAGGAGCTGA CCAGTGAAGC AAGTGTCTTT
    GAAGTCTTTG TTCTTTACCT CTCGGGAGAA CCAAACCGGA ATGGTCACAA Agtgagtgat
    gctggaagtg gggaccctgg ttcatccct gccctggcc t
```

EXON 8: 183 bp        (bp 1360-1542)

```
    cagggtgcca aacctgatgg tcgcccagc cagctcaccg tctctcccag GTGACTTGCC
    TGCCCTGGAA CGATGAGCCC CTGGCGGCTG AGACCAGCCT GCTGAAGGAG GAGCTGCTGC
    GGGTGAACCG CCAGGGCATC CTCACCATCA ACTCACAGCC CAACATCAAC GGGAAGCCGT
    CCTCCGACCC CATCGTGGGC TGGGCCCCA GCGGGGGCTA TGTCTTCCAG AAGgtgtggt
    agggaggcac ggggtgcccc cctctcttga ccggcaccg tgg
```

EXON 9: 102 bp        (bp 1543-1644)

```
    gggcgtctgg cagggctggg gttggtgaca ggcacctgtc tctcccacag GCCTACTTAG
    AGTTTTTCAC TTCCGCGAG ACAGCGGAAG CACTTCTGCA AGTGCTGAAG AAGTACGAGC
    TCCGGGTTAA TTACCACCTT GTCAATGTGA AGgtaggcca ggccccacgg ttcccacaga
    gtaccaggcc cttcgttgaa ca
```

EXON 10: 120 bp       (bp 1645-1764)

```
    actccagttg ttcttggccc aggtcttacc cccacccac atccctcag GGTGAAAACA
    TCACCAATGC CCCTGAACTG CAGCCGAATG CTGTCACTTG GGGCATCTTC CCTGGGCGAG
    AGATCATCCA GCCCACCGTA GTGGATCCCG TCAGCTTCAT GTTCTGGAAG gtaaaggagc
    gggggcaagc ttgccccgcc cacctggaaa accgtgggga
```

EXON 11: 219 bp (stop codon)   (bp 1765-1983)
       432 bp (end of cDNA)    (bp 1765-2196)

```
    ctctgtgtgt gtgtgcatgt gtgcgtgtgt gcggggggtat gtgtgtgtag GACGAGGCCT
    TTGCCCTGTG GATTGAGCGG TGGGAAAGC TGTATGAGGA GGAGTCCCCG TCCCGCACCA
    TCATCCAGTA CATCCACGAC AACTACTTCC TGGTCAACCT GGTGGACAAT GACTTCCCAC
    TGGACAACTG CCTCTGGCAG GTGGTGGAAG ACACATTGGA GCTTCTCAAC AGGCCCACCC
    AGAATGCGAG AGAAACGGAG GCTCCATGAC CCTGCGTCCT GACGCCCTGC GTTGGAGCCA
    CTCCTGTCCC GCCTTCCTCC TCCACAGTGC TGCTTCTCTT GGGAACTCCA CTCTCCTTCG
    TGTCTCTCCC ACCCCGGCCT CCACTCCCCC ACCTGACAAT GGCAGCTAGA CTGGAGTGAG
    GCTTCCAGGC TCTTCCTGGA CCTGAGTCGG CCCCACATGG GAACCTAGTA CTCTCTGCTC
    TAgccaggag tctgtgctct tttggtgggg agcacttgct cctgcagagg ac
```

Figure 2B

A
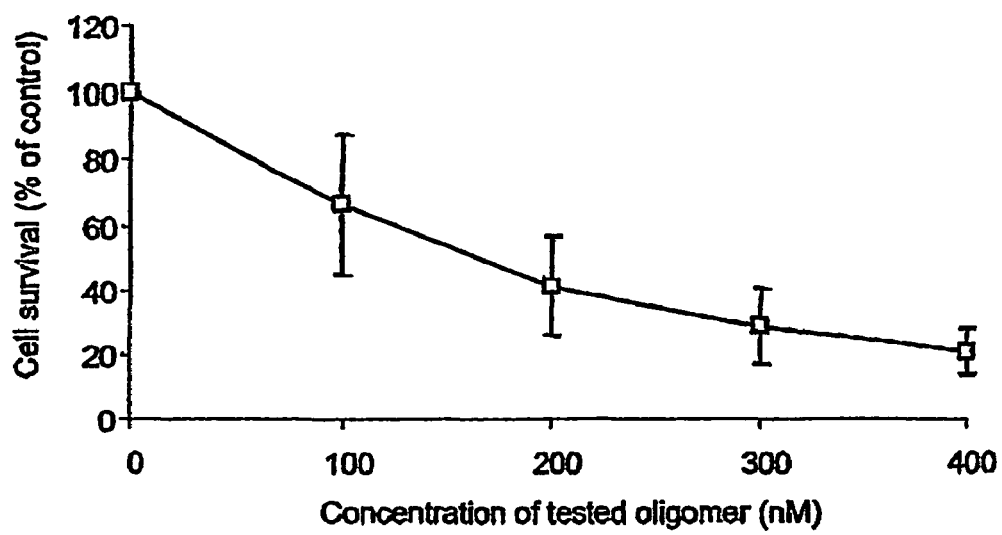
B
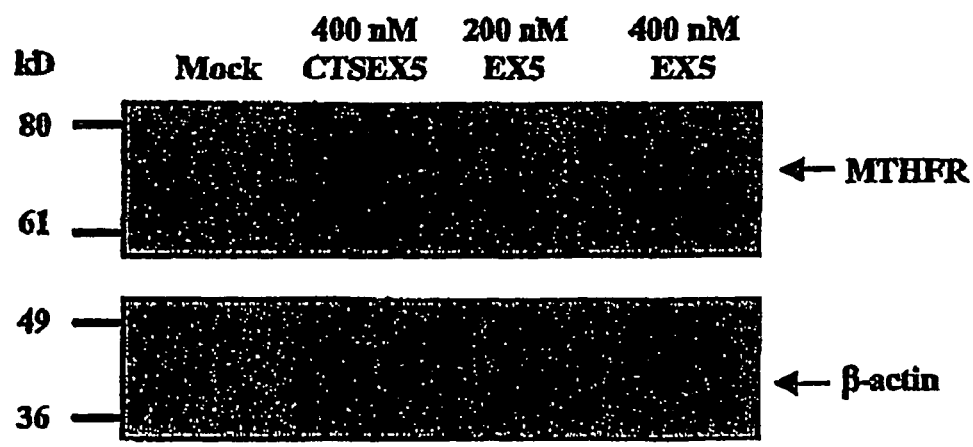
Figure 12

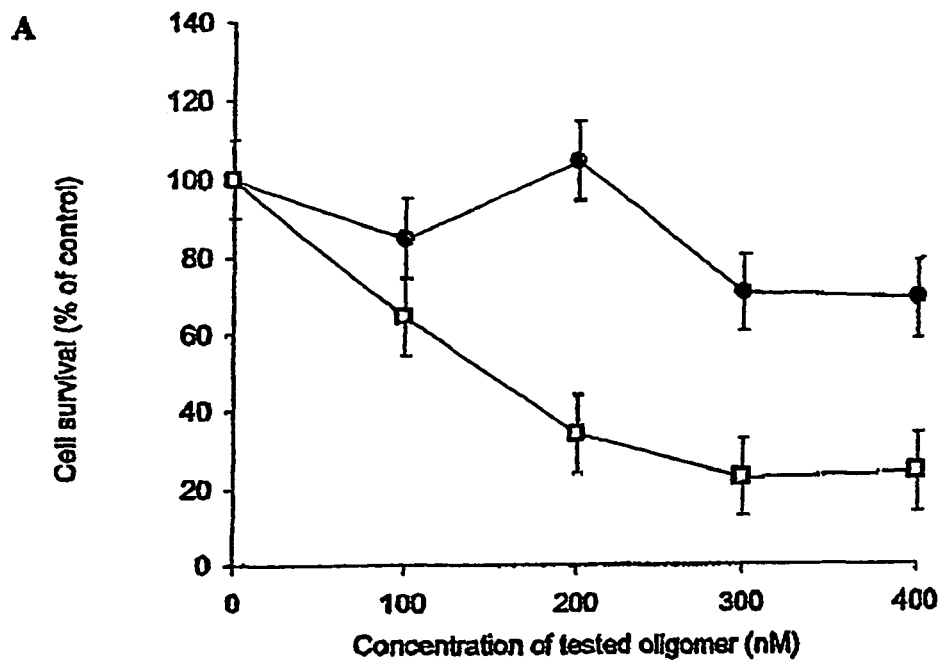
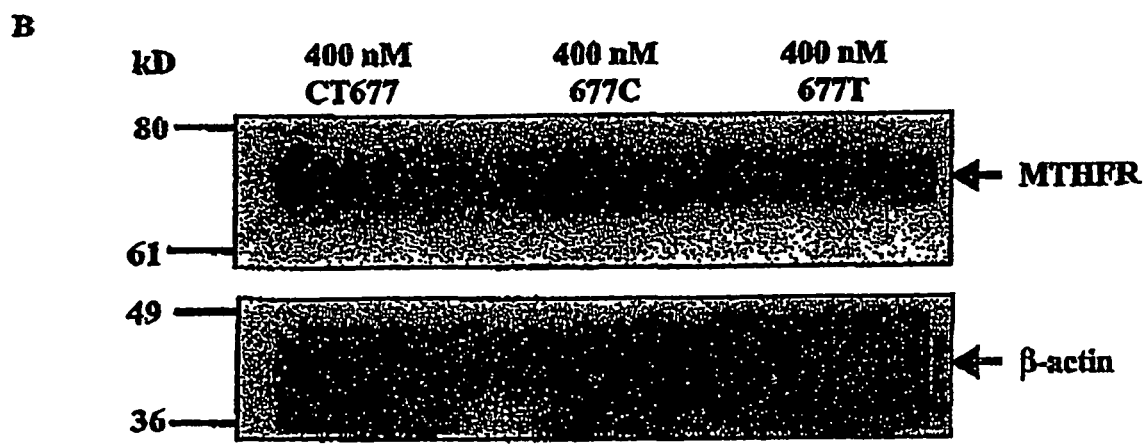
Figure 13

METHYLENETETRAHYDROFOLATE REDUCTASE INHIBITORS AND USE THEREOF

The application disclosed herein corresponds to International Application No. PCT/CA01/01697, filed Dec. 3, 2001, which claims priority of U.S. Ser. No. 09/728,910, filed Dec. 1, 2000, now abandoned, the contents of which are hereby incorporated by reference into this application. Throughout this invention, various references are cited. Disclosures of these publications in their entireties are hereby incorporated by reference into this application to describe more fully the state of the art to which this invention pertains.

FIELD OF THE INVENTION

The present invention pertains to the field of inhibitors of cancer cell growth and/or metastasis. More particularly the present invention pertains to inhibitors of methylenetetrahydrofolate reductase and use thereof in the treatment of cancer.

BACKGROUND

Folic acid derivatives are coenzymes for several critical single-carbon transfer reactions, including reactions in the biosynthesis of purines, thymidylate and methionine. Methylenetetrahydrofolate reductase (MTHFR; EC 1.5.1.20) catalyses the NADPH-linked reduction of 5,10-methylenetetrahydrofolate to 5-methyltetrahydrofolate, a co-substrate for methylation of homocysteine to methionine.

Hereditary deficiency of MTHFR, an autosomal recessive disorder, is the most common inborn error of folic acid metabolism. A block in the production of methyltetrahydrofolate leads to elevated homocysteine with low to normal levels of methionine. Patients with severe deficiencies of MTHFR (0-20% activity in fibroblasts) can have variable phenotypes. Developmental delay, mental retardation, motor and gait abnormalities, peripheral neuropathy, seizures and psychiatric disturbances have been reported in this group, although at least one patient with severe MTHFR deficiency was asymptomatic. Pathologic changes in the severe form include the vascular changes that have been found in other conditions with elevated homocysteine, as well as reduced neurotransmitter and methionine levels in the CNS. A milder deficiency of MTHFR (35-50% activity) has been described in patients with coronary artery disease (see below). Genetic heterogeneity is likely, considering the diverse clinical features, the variable levels of enzyme activity, and the differential heat inactivation profiles of the reductase in patients' cells.

MTHFR isolated from porcine liver has been purified to homogeneity and has been found to be a homodimer of 77-kDa subunits. Partial proteolysis of the porcine peptide has revealed two spatially distinct domains: an N-terminal domain of 40 kDa and a C-terminal domain of 37 kDa. The latter domain contains the binding site for the allosteric regulator S-adenosylmethionine.

The cDNA for human MTHFR has been isolated and mapped, and mutations in the gene have been identified in MTHFR-deficient individuals (Goyette, et al., (1994) *Nat. Genet.,* 7:195-200). International Patent Application No. PCT/IB00/00442 discloses nucleic acid probes for the MTHFR gene, methods of identifying mutations in the MTHFR gene of individuals with MTHFR deficiency and methods of treatment for individuals with MTHFR deficiency involving the provision of a functional MTHFR gene or protein. The application further teaches that the MTHFR deficiency may be associated with a disease, disorder or dysfunction including cancers such as neuroblastomas and colorectal carcinomas.

PCT/IB00/00442 also postulates about a method for treating a patient having a cancer by inhibiting MTHFR gene expression or by inhibiting the MTHFR protein. However, given the teaching therein, it remains uncertain whether such a method would be effective in the treatment of cancer especially in view of the demonstrated link between MTHFR deficiency and disease. PCT/IB00/00442 does not discuss how the treatment of a patient having a cancer by inhibiting MTHFR gene expression or the MTHFR protein could be implemented or what effect such inhibition may have on cancer cells. In fact, PCT/IB00/00442 appears to teach that reducing MTHFR activity in a subject will have a deleterious effect.

There remains, therefore, a need for a method of selectively targeting cancer cells. In particular for a method that provides specific inhibition of the growth of cancer cells.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are hereby incorporated by reference in their entireties in this application.

SUMMARY OF THE INVENTION

An object of the present invention is to provide methylenetetrahydrofolate reductase inhibitors and use thereof. In accordance with an aspect of the present invention, there is provided an inhibitor of methylenetetrahydrofolate reductase (MTHFR) for use in selective inhibition of cancer cell growth in a mammal in need of such therapy, wherein the inhibitor reduces MTHFR gene expression or MTHFR activity.

In accordance with another aspect of the invention, there is provided a nucleic acid comprising a sequence encoding an inhibitor of methylenetetrahydrofolate reductase (MTHFR) for use in selective inhibition of cancer cell growth in a mammal in need of such therapy, wherein the inhibitor reduces MTHFR gene expression or MTHFR activity and wherein the inhibitor is an antisense oligonucleotide, a ribozyme, a triple helix forming oligonucleotide, an anti-MTHFR antibody or fragment thereof, an MTHFR mutant or a fragment of MTHFR. In accordance with yet another aspect of the invention there is provided a vector comprising this nucleic acid.

In accordance with another aspect of the invention, there is provided a pharmaceutical composition comprising an inhibitor of methylenetetrahydrofolate reductase (MTHFR) for use in selective inhibition of cancer cell growth in a mammal in need of such therapy, wherein the inhibitor reduces MTHFR gene expression or MTHFR activity and a pharmaceutically acceptable carrier, diluent or excipient.

In accordance with another aspect of the invention, there is provided a use of an MTHFR inhibitor for the manufacture of a medicament, wherein the inhibitor selectively inhibits cancer cell growth and wherein the inhibitor reduces MTHFR gene expression or MTHFR activity.

In accordance with another aspect of the invention, there is provided a use of a vector comprising a nucleic acid comprising a sequence encoding an inhibitor of methylenetetrahydrofolate reductase (MTHFR) for use in selective inhibition of cancer cell growth in a mammal in need of such therapy, wherein the inhibitor reduces MTHFR gene expression or MTHFR activity and wherein the inhibitor is an antisense oligonucleotide, a ribozyme, a triple helix forming oligonucleotide, an anti-MTHFR antibody or fragment thereof, an MTHFR mutant or a fragment of MTHFR, for the manufacture of a medicament, wherein the inhibitor selectively inhibits cancer cell growth and wherein the inhibitor reduces MTHFR gene expression or MTHFR activity.

In accordance with another aspect of the invention, there is provided a use of a non-allele specific antisense oligonucleotide at least 7 nucleotides in length that comprises a sequence that is complementary to a gene encoding human MTHFR, wherein the oligonucleotide inhibits human MTHFR gene expression. In accordance with yet another aspect of the invention, there is provided a vector comprising a sequence encoding this antisense oligonucleotide.

In accordance with another aspect of the invention, there is provided a method of treating stabilizing or preventing cancer in a mammal comprising the step of selectively inhibiting cancer cell growth in the mammal by administering an inhibitor of MTHFR, wherein the inhibitor reduces MTHFR gene expression or MTHFR activity.

In accordance with another aspect of the invention, there is provided a method of inhibiting growth of cancer cells comprising the step of contacting said cancer cells with an inhibitor of MTHFR, wherein the inhibitor does not significantly affect non-cancerous cell growth and wherein the inhibitor reduces MTHFR gene expression or MTHFR activity.

In accordance with another aspect of the invention, there is provided a kit for the use of an MTHFR inhibitor for the manufacture of a medicament or the methods of the present invention, comprising an inhibitor of MTHFR which selectively inhibits cancer cell growth, wherein the inhibitor reduces MTHFR gene expression or MTHFR activity.

BRIEF DESCRIPTION OF THE FIGURES

FIG. 1 depicts the total available sequence (SEQ ID NO:1 and NO:2) of human MTHFR cDNA.

FIG. 2 depicts human MTHFR exons and flanking intronic sequences. The exonic sequences (SEQ ID NOs:3-13) of the human gene are given, along with their sizes and flanking intronic sequences. The base pair location of the exons within the cDNA, given in parenthesis, relates to the published human cDNA base pair numbering (Goyette et al., 1994). Base 1 is 12 bp upstream from the ATG in original cDNA, the equivalent base is indicated here by an asterisk. Exon 1 contains the ATG start site (underlined), and exon 11 contains the termination codon (underlined).

FIG. 12 depicts the growth of colon carcinoma cell lines in deficient media. Four colon carcinoma cell lines were grown in MEM (■), M– (×), and M–H+ (μ) for 12 days. The MTHFR genotype of each colon carcinoma cell line is indicated in parentheses. The number of cells for each line was counted using the SRB assay at 3 time points. Each point represents the mean of 3 replicates ±SD.

FIG. 13 depicts cell survival and MTHFR protein levels after treatment with the antisense oligonucleotide EX5. (A) Cells were treated on three successive days with increasing concentration of EX5 (o). Cells were also treated with a control oligonucleotide, CTSEX5. The number of surviving cells was determined by SRB staining. Cell survival after transfection with EX5 is expressed as a % of survival after transfection with the control CTSEX5 oligonucleotide. Error bars represent ±SE of the mean of 3 experiments, each performed in triplicate. (B) MTHFR protein levels after three rounds of treatments with Lipofectin only (mock transfection), 400 nM of CTSEX5, 200 nM of EX5 or 400 nM of EX5. Cells were harvested after the third treatment and subjected to Western blot analysis. The position of the MTHFR protein and the molecular weight markers are indicated. Protein levels of β-actin were also assayed by Western blotting to verify equal loading of samples.

DETAILED DESCRIPTION OF THE INVENTION

Figure 3:
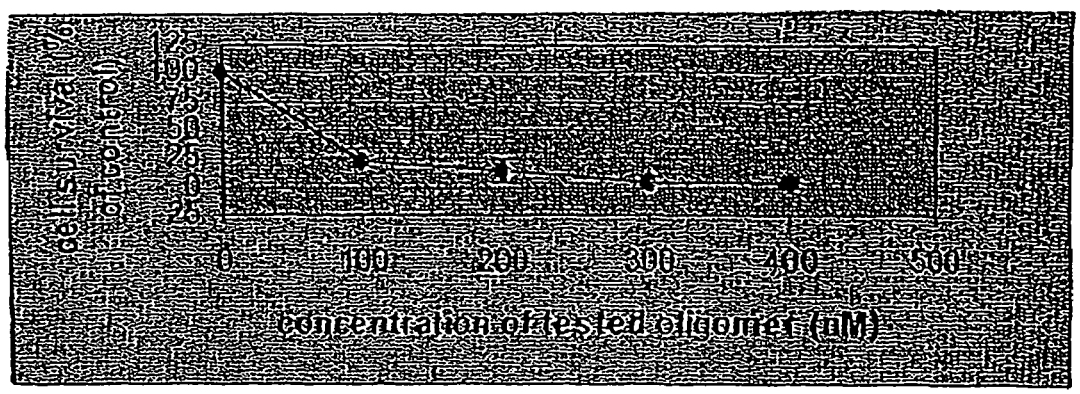
FIG. 3 demonstrates the percent survival of SW620 colon carcinoma cells following three rounds of treatment for five hours each round with varying concentrations of an antisense phosphorothioate oligonucleotide to exon 5 of MTHFR. The cells were allowed to recover after the final treatment for a period of two days before the cells were counted. The values are expressed as the percent of cells surviving compared to the number of cells which survived after treatment with a control oligonucleotide CTSEX5 (phosphorothioate 5'-GTGACGTAGGACAGCGATGG-3'; SEQ ID NO:17).
Figure 4:
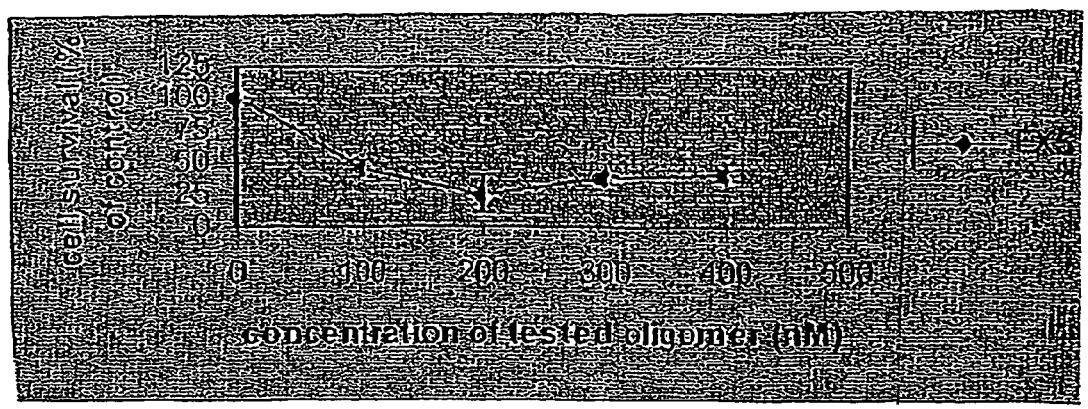
FIG. 4 demonstrates the percent survival of LOVO colon carcinoma cells treated with an MTHFR antisense oligonucleotide after a recovery period of three days, as described for FIG. 3.
Figure 5:
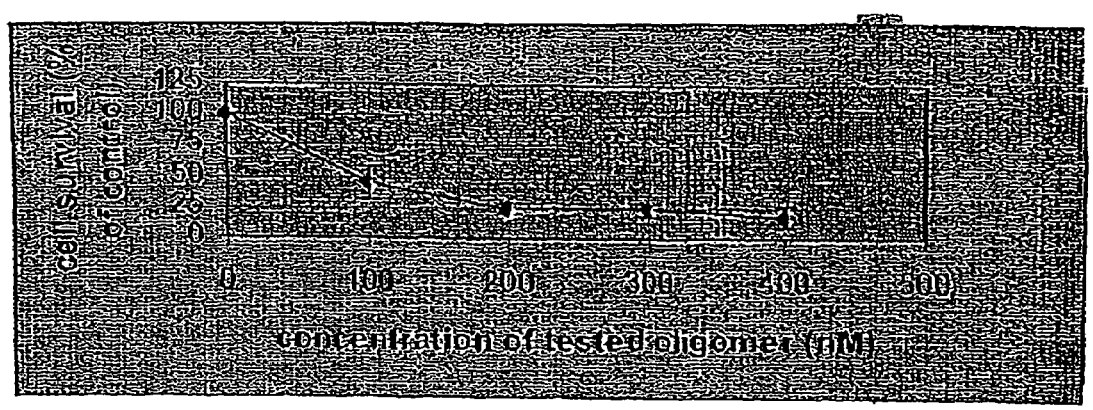
FIG. 5 demonstrates the percent survival of BEC 2 neuroblastoma cells treated with varying concentrations of an MTHFR antisense oligonucleotide and allowed to recover for two days, as described for FIG. 3.
Figure 6:
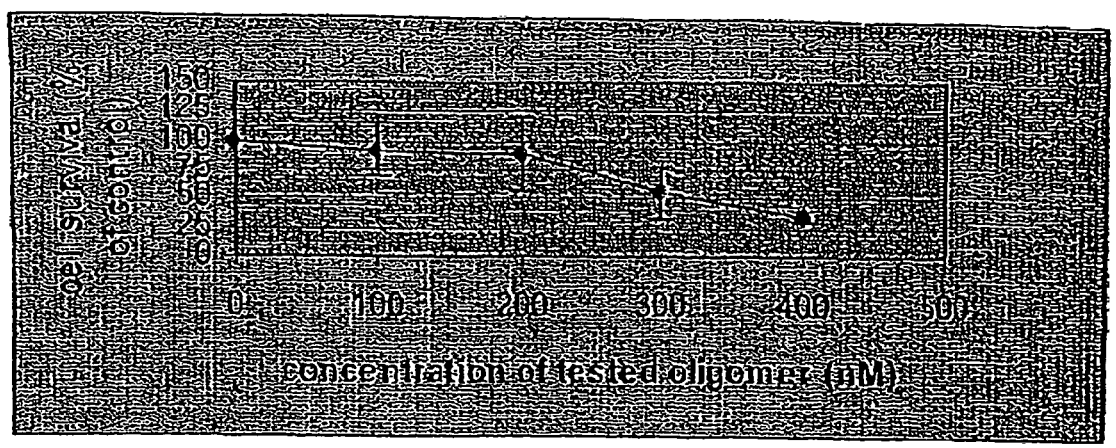
FIG. 6 demonstrates the percent survival of SK-N-F1 neuroblastoma cells treated with varying concentrations of an MTHFR antisense oligonucleotide after a recovery period of four days, as described for FIG. 3.
Figure 7:
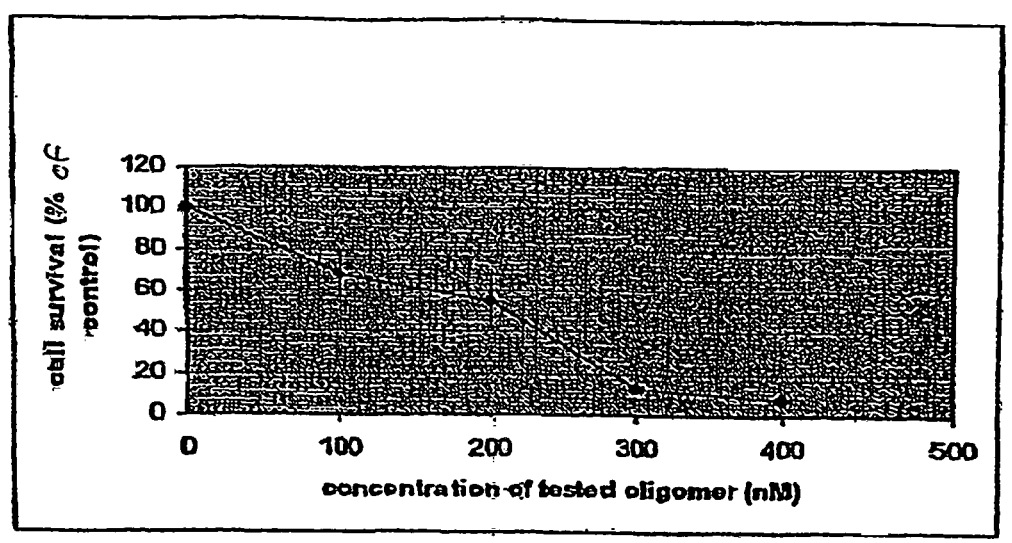
FIG. 7 demonstrates the percent survival of MCF7 breast cancer cells that were treated with different concentrations of an MTHFR antisense oligonucleotide and allowed to recover for 2.5 days, as described for FIG. 3.
Figure 8:
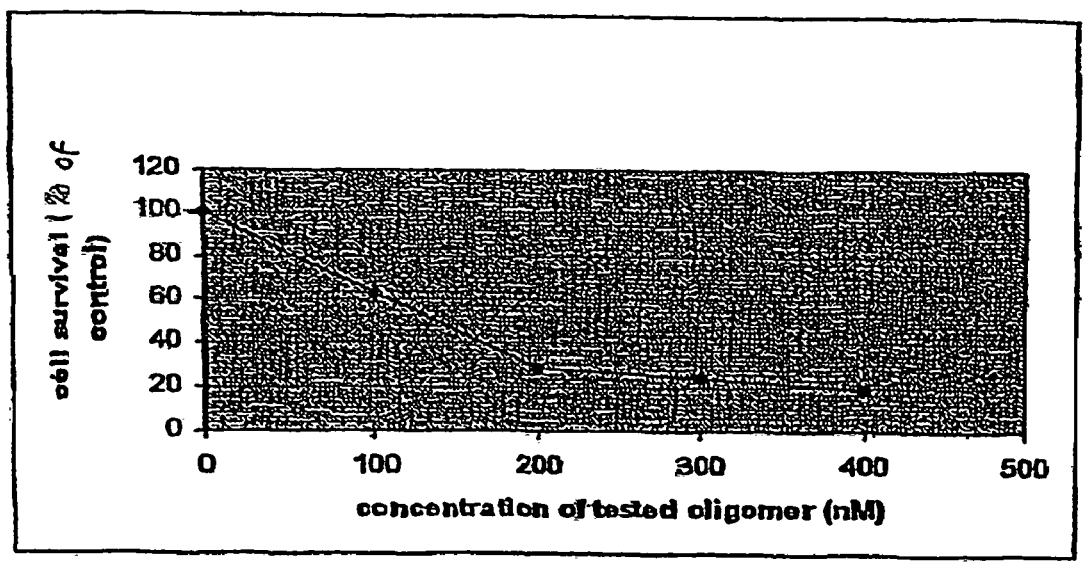
FIG. 8 demonstrates the percent survival of SKBr3 breast cancer cells treated with varying concentrations of an MTHFR antisense oligonucleotide after a recovery period of 2.5 days, as described for FIG. 3.
Figure 9:
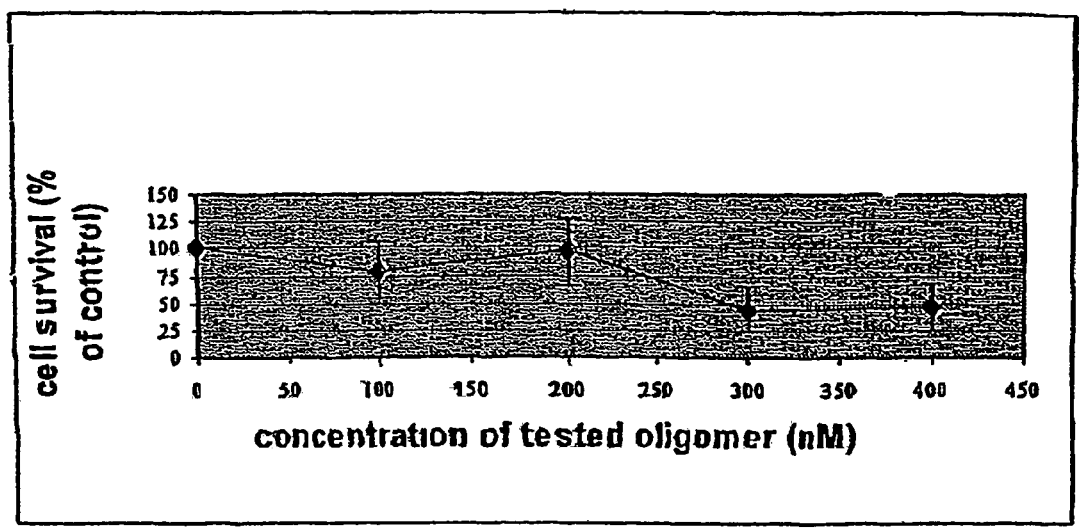
FIG. 9 demonstrates the percent survival of U87-lacZ glioma cells treated with varying concentrations of an MTHFR antisense oligonucleotide after a recovery period of two days, as described for FIG. 3. For this experiment an oligonucleotide with six base pair mismatches CT677 (phosphorothioate 5'-TGCTGTCGGAGCGATAGGTC-3'; SEQ ID NO:18) was used as the control oligonucleotide.

The present invention provides a method of selectively inhibiting the growth of cancer cells by downregulating MTHFR activity. In the context of the present invention, downregulation of MTHFR activity can be achieved by direct inhibition of the MTHFR protein, or by inhibition of MTHFR gene expression.

In view of the prior art regarding the deleterious effects of MTHFR deficiency, a downregulation of levels of MTHFR protein would be expected to produce only negative effects. Therefore, a particularly unexpected result of downregulation of MTHFR protein levels in a mouse cancer model was its effectiveness in reducing the number and size of tumours. As described herein, this unexpected finding was further demonstrated following inhibition of MTHFR gene expression using non-allele specific antisense oligonucleotides in the treatment of cancer cells and of normal cells.

Definitions

Unless defined otherwise, all technical and scientific terms used herein have the same meaning as commonly understood by one of ordinary skill in the art to which this invention pertains.

The term "non allele-specific" as used herein refers to a compound capable of binding to at least two different MTHFR alleles.

The term "specifically hybridize" as used herein refers to the ability of a nucleic acid to bind detectably and specifically to a second nucleic acid. Polynucleotides, oligonucleotides and fragments thereof specifically hybridize to target nucleic acid strands under hybridization and wash conditions that minimize appreciable amounts of detectable binding to nonspecific nucleic acids. High stringency conditions can be used to achieve specific hybridization as known in the art (for example, see Ausubel, et al., (2000) *Current Protocols in Molecular Biology*, Wiley & Sons, New York, N.Y.).

Typically, hybridization and washing conditions are performed at high stringency according to conventional hybridization procedures. Washing conditions are typically 1-3× SSC, 0.1-1% SDS, 50-70$^E$C, with a change of wash solution after about 5-30 minutes.

The term "corresponds to" as used herein with reference to nucleic acid sequences means a polynucleotide sequence that is identical to all or a portion of a reference polynucleotide sequence. In contradistinction, the term "complementary to" is used herein to mean that the polynucleotide sequence is identical to all or a portion of the complement of a reference polynucleotide sequence. For illustration, the nucleotide sequence "TATAC" corresponds to a reference sequence "TATAC" and is complementary to a reference sequence "GTATA."

The following terms are used herein to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e. a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e. gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (U.S.A.) 85:2444, by computerized implementations of these algorithms (GAP, BESTFIT, FASTA, and TFASTA in the Wisconsin Genetics Software Package Release 7.0, Genetics Computer Group, 573 Science Dr., Madison, Wis.), or by inspection, and the best alignment (i.e. resulting in the highest percentage of homology over the comparison window) generated by the various methods is selected.

The term "sequence identity" means that two polynucleotide sequences are identical (i.e. on a nucleotide-by-nucleotide basis) over the window of comparison. The term "percentage of sequence identity" is calculated by comparing two optimally aligned sequences over the window of comparison, determining the number of positions at which the identical nucleic acid base (e.g. A, T, C, G, U, or I) occurs in both sequences to yield the number of matched positions, dividing the number of matched positions by the total number of positions in the window of comparison (i.e. the window size), and multiplying the result by 100 to yield the percentage of sequence identity.

The term "substantial identity" as used herein denotes a characteristic of a polynucleotide sequence, wherein the polynucleotide comprises a sequence that has at least 30 percent sequence identity, often at least 50 percent sequence identity, and more usually at least 60 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison.

MTHFR Inhibitors

The present invention provides compounds that selectively inhibit the growth of cancer cells by downregulating MTHFR activity in a mammal (e.g., a human). The extent of selective inhibition is generally sufficient to treat, stabilize, or prevent cancer in the mammal. In the context of the present invention, selective inhibition means that the growth of cancer cells is inhibited substantially more than the growth of normal cells. In a specific embodiment of the present invention cancer cell growth is inhibited by an MTHFR inhibitor under conditions in which the growth of normal cells also treated with the MTHFR inhibitor is fully or partially unaffected. When the growth of normal cells is partially affected by contact with the MTHFR inhibitor, the difference between the affect on cancer cells and on normal cells is such that the cancer cells are preferentially inhibited and/or killed by contact with the MTHFR inhibitor.

The inhibitors according to the present invention can be antisense oligonucleotides, biologically inactive MTHFR proteins or fragments, peptides, small molecule inhibitors or antibodies.

(i) Antisense Oligonucleotides

"Targeting" an antisense compound to a particular nucleic acid, in the context of this invention, is a multistep process. The process usually begins with the identification of a nucleic acid sequence whose function is to be modulated. In the present invention, the target is the gene encoding MTHFR. The targeting process also includes determination of a site or sites within this gene for the antisense interaction to occur such that the desired effect, i.e. modulation of expression of the protein encoded by the gene, will result.

Generally, there are five regions of a gene that may be targeted for antisense modulation: the 5' untranslated region (5'-UTR), the translation initiation or start codon region, the open reading frame (ORF), the translation termination or stop codon region and the 3' untranslated region (3'-UTR).

The terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding MTHFR regardless of the sequence(s) of such codons.

As is known in the art, some eukaryotic transcripts are directly translated, however, most mammalian ORFs contain one or more sequences, known as "introns," which are excised from a transcript before it is translated; the expressed (unexcised) portions of the ORF are referred to as "exons" (Alberts et al., (1983) *Molecular Biology of the Cell*, Garland Publishing Inc., New York, pp. 411-415). In the context of the present invention, both introns and exons may serve as targets for antisense.

In some instances, an ORF may also contain one or more sites that may be targeted for antisense due to some functional significance in vivo. Examples of the latter types of sites include intragenic stem-loop structures (see, for example, U.S. Pat. No. 5,512,438) and, in unprocessed mRNA molecules, intron/exon splice sites. In addition, mRNA molecules possess a 5' cap region that may also serve as a target for antisense. The 5' cap of a mRNA comprises an $N^7$-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap.

In accordance with the present invention, the antisense oligonucleotides are non allele-specific, therefore, regions of the gene to be targeted are those that are conserved, i.e. show no sequence difference, among the different alleles of the MTHFR gene. In one embodiment of the present invention, the antisense oligonucleotides are targeted to all or part of one of exons 1-11 or other MTHFR exon (Goyette et al., (1998) *Mammalian Genome* 9:652-656). In a related embodiment, the antisense oligonucleotides are targeted to exon 5 of the MTHFR gene. In a further related embodiment of the present invention, the antisense oligonucleotide has the sequence 5'-AGCTGCCGAAGGGAGTGGTA-3' (SEQ ID NO:16) and binds to nucleotides 796-815 of exon 5 of the MTHFR gene.

In accordance with the present invention, the antisense oligonucleotide binds at least 70% of the human MTHFR alleles. In a related embodiments the antisense oligonucleotide binds at least 80%, or at least 90% of the human MTHFR alleles. In another embodiment of the present invention, the antisense nucleic acid does not bind to a region of the MTHFR gene that contains a polymorphic site.

Once the target site or sites have been identified, oligonucleotides are chosen that are sufficiently complementary (i.e. hybridize with sufficient strength and specificity) to the target to give the desired result.

The antisense oligonucleotides in accordance with the present invention are selected from a sequence complementary to the MTHFR gene such that the sequence exhibits the least likelihood of forming duplexes, hair-pins, or of containing homooligomer/sequence repeats. The oligonucleotide may further contain a GC clamp. These properties can be determined qualitatively using commercially available computer software, for example, the computer modeling program OLIGO® Primer Analysis Software, Version 5.0 (distributed by National Biosciences, Inc., Plymouth, Minn.).

In order to be effective, antisense oligonucleotides are typically between 7 and 350 nucleotides in length. In one embodiment of the present invention the antisense oligonucleotides comprise from at least about 7 to about 50 nucleotides, or nucleotide analogues. In related embodiments the antisense oligonucleotides comprise from about 15 to about 25 nucleotides, or nucleotide analogues, or from about 18 to about 22 nucleotides, or nucleotide analogues.

It is understood in the art that an antisense oligonucleotide need not have 100% identity with its target sequence. The present invention, therefore, contemplates antisense oligonucleotides that have 100% sequence identity with the target sequence as well as those that have a sequence that is at least about 75% identical to the target sequence. In one embodiment of the present invention, the antisense oligonucleotides have a sequence that is at least about 90% identical. In a related embodiment, they have a sequence that is at least about 95% identical with the target sequence, allowing for gaps or mismatches of several bases. In accordance with the present invention, the antisense oligonucleotide is less than 50% identical to the reverse complement of a region in another human expressed sequence (EST) or, in other reported human ESTs. Identity can be determined, for example, by using the BLASTN program of the University of Wisconsin Computer Group (GCG) software.

Alternatively an antisense oligonucleotide of the present invention can be defined by its ability to specifically hybridize to the target MTHFR gene, as determined using standard techniques known to workers skilled in the art (e.g. hybridization assays).

In the context of the present invention, the term "oligonucleotide" refers to an antisense oligomer or polymer of ribonucleic acid (RNA), deoxyribonucleic acid (DNA), modified RNA or DNA, or RNA or DNA mimetics. This term, therefore, includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, enhanced cellular uptake, enhanced affinity for nucleic acid target and increased stability in the presence of nucleases.

Examples of modified or substituted antisense compounds useful in this invention include oligonucleotides containing modified backbones or non-natural internucleoside linkages. In accordance with the present invention, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Exemplary modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA) (Nielsen et al., (1991) *Science*, 254:1497-1500). In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

Modified oligonucleotides may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2CH_2OCH_3$, also known as 2'-O-(2-methoxyethyl) or 2'-MOE) (Martin et al., (1995) *Helv. Chim. Acta*, 78:486-504), 2'-dimethylaminooxyethoxy ($O(CH_2)_2$ $ON(CH_3)_2$ group, also known as 2'-DMAOE), 2'-methoxy (2'-O—$CH_3$), 2'-aminopropoxy (2'-$OCH_2CH_2CH_2NH_2$) and 2'-fluoro (2'-F).

Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethylcytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., (1991) *Angewandte Chemie, Int. Ed.*, 30:613; and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., (1993) *Antisense Research and Applications*, pp 276-278, Crooke, S. T. and Lebleu, B., ed., CRC Press, Boca Raton).

Another oligonucleotide modification included in the present invention is to chemically link to the oligonucleotide one or more moieties or conjugates which enhance the activity, cellular distribution or cellular uptake of the oligonucleotide. Such moieties include, but are not limited to, lipid moieties such as a cholesterol moiety (Letsinger et al., (1989) *Proc. Natl. Acad. Sci. USA*, 86:6553-6556), cholic acid (Manoharan et al., (1994) *Bioorg. Med. Chem. Let.*, 4:1053-1060), a thioether, e.g. hexyl-S-tritylthiol (Manoharan et al., (1992) *Ann. N.Y. Acad. Sci.,* 660:306-309; Manoharan et al., (1993) *Bioorg. Med. Chem. Lett.,* 3:2765-2770), a thiocholesterol (Oberhauser et al., (1992) *Nucl. Acids Res.,* 20:533-538), an aliphatic chain, e.g. dodecandiol or undecyl residues (Saison-Behmoaras et al., (1991) *EMBO J.,* 10:1111-1118; Kabanov et al., (1990) *FEBS Lett.,* 259:327-330; Svinarchuk et al., (1993) *Biochimie,* 75:49-54), a phospholipid, e.g. di-hexadecyl-rac-glycerol or triethylammonium 1,2-di-O-hexadecyl-rac-glycero-3-H-phosphonate (Manoharan et al., (1995) *Tetrahedron Lett.,* 36:3651-3654; Shea et al., (1990) *Nucl. Acids Res.,* 18:3777-3783), a polyamine or a polyethylene glycol chain (Manoharan et al., (1995) *Nucleosides & Nucleotides,* 14:969-973), or adamantane acetic acid (Manoharan et al., (1995) *Tetrahedron Lett.,* 36:3651-3654), a palmityl moiety (Mishra et al., (1995) *Biochim. Biophys. Acta,* 1264:229-237), or an octadecylamine or hexylamino-carbonyl-oxycholesterol moiety (Crooke et al., (1996) *J. Pharmacol. Exp. Ther.,* 277:923-937).

One skilled in the art will recognise that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide. The present invention further includes antisense compounds that are chimeric compounds. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

In the context of the present invention, an antisense oligonucleotide is "nuclease resistant" when it has either been modified such that it is not susceptible to degradation by DNA and RNA nucleases or alternatively has been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes.

The present invention further contemplates antisense oligonucleotides that contain groups for improving the pharmacokinetic properties of the oligonucleotide, or groups for improving the pharmacodynamic properties of the oligonucleotide.

In one embodiment of the present invention, the antisense oligonucleotide is a phosphorothioate nucleic acid in which a non-bridging phosphoryl oxygen in one or more of the nucleotides is replaced with sulphur. In a related embodiment, the antisense oligonucleotide is the phosphorothioate oligonucleotide with the sequence 5'-AGCTGCCGAAGG-GAGTGGTA-3' (SEQ ID NO:16), which binds to exon 5 of the MTHFR gene.

The antisense oligonucleotides of the present invention can be prepared by conventional techniques well-known to those skilled in the art. For example, the oligonucleotides can be prepared using solid-phase synthesis using commercially available equipment, such as the equipment available from Applied Biosystems Canada Inc., Mississauga, Canada. As is well-known in the art, modified oligonucleotides, such as phosphorothioates and alkylated derivatives, can also be readily prepared by similar methods.

Alternatively, the antisense oligonucleotides of the present invention can be prepared by enzymatic digestion of the naturally occurring MTHFR gene by methods known in the art.

Antisense oligonucleotides can also be prepared by recombinant DNA techniques. The present invention, therefore, encompasses expression vectors comprising nucleic acid sequences that encode one or more antisense oligonucleotide that targets the MTHFR gene. The antisense oligonucleotide(s) encoded by such expression vectors is expressed in a suitable host cell. Suitable expression vectors can be readily constructed using procedures known in the art. Examples of suitable vectors include, but are not limited to, plasmids, phagemids, cosmids, bacteriophages, baculoviruses, retroviruses, and RNA and DNA viruses. Generally, the viral vectors are replication deficient by are capable of expression f the antisense oligonucleotide(s).

One skilled in the art will understand that selection of the appropriate host cell for expression of the antisense oligonucleotide will be dependent upon the vector chosen. Examples of host cells include, but are not limited to, bacterial, yeast, insect, plant and mammalian cells.

One skilled in the art will also understand that the expression vector may further include regulatory elements required for efficient transcription or translation of the antisense oligonucleotide sequences. Examples of regulatory elements that can be incorporated into the vector include, but are not limited to, transcriptional elements such as promoters, enhancers, terminators, and polyadenylation signals. The present invention, therefore, provides vectors comprising one or more regulatory elements operatively linked to a nucleic acid sequence encoding an antisense oligonucleotide. One skilled in the art will appreciate that selection of suitable regulatory elements is dependent on the host cell chosen for expression of the antisense oligonucleotide and that such elements may be derived from a variety of sources, including bacterial, fungal, viral, mammalian or insect genes.

In the context of the present invention, the expression vector may additionally contain a reporter gene. Suitable reporter genes include, but are not limited to, β-galactosidase, green fluorescent protein, red fluorescent protein, luciferase, and β-glucuronidase. Incorporation of a reporter gene into the expression vector allows transcription of the antisense oligonucleotide to be monitored by detection of a signal generated by expression of the reporter gene.

In accordance with the present invention, the expression vectors can be introduced into a suitable host cell or tissue by one of a variety of methods known in the art. These methods include, for example, stable or transient transfection, lipofection, electroporation, and infection with recombinant viral vectors. Methods of constructing expression vectors and introducing these vectors into host cells are well-known in the art, and are generally described in Sambrook et al., (1992) *Molecular Cloning: A Laboratory*

*Manual,* Cold Spring Harbor Press; Ausubel et al., (2000) *Current Protocols in Molecular Biology,* Wiley & Sons, New York.

In a related embodiment of the present invention the MTHFR inhibitor is an oligonucleotide that hybridizes to and forms triple helix structures at the 5' terminus of the MTHFR gene and can be used to block transcription. The triple helix forming oligonucleotides can be prepared as described above in relation to the antisense oligonucleotides. Similarly, nucleic acids encoding the triple helix forming oligonucleotide can be cloned into a vector as described above.

The ability of the antisense oligonucleotides or triple helix forming oligonucleotides of the present invention to inhibit MTHFR gene expression can be determined by a number of techniques known to one skilled in the art. For example, the level of MTHFR mRNA can be determined by standard Northern blot analysis, and/or the level of MTHFR protein can be determined by standard Western blot analysis. Methods of conducting these methods are well-known to workers skilled in art (see, for example, Ausubel et al., (2000) *Current Protocols in Molecular Biology,* Wiley & Sons, New York: Coligan, et al., (2001) *Current Protocols in Protein Science,* Wiley & Sons, New York). In one embodiment of the present invention, the level of MTHFR protein is determined by measuring the level of MTHFR enzymatic activity, as described in Christensen, et al., (1997) *Arterioscler. Thromb. Vasc. Bio.,* 17:573-596. In an alternate embodiment, the level of MTHFR protein can be assessed by measuring the resulting increase in cellular levels of homocysteine, or decrease in 5-methyltetrahydrofolate or methionine, as described herein.

(ii) Ribozymes

In one embodiment of the present invention the MTHFR inhibitor is a ribozyme that specifically targets RNA encoding MTHFR. Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 Proc. Nati. Acad. Sci. USA 8788, 1987; Haseloff and Gerlach, 334 Nature 585, 1988; Cech, 260 JAMA 3030, 1988; and Jefferies et al., 17 Nucleic Acids Research 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

Hammerhead ribozymes comprise a hybridizing region which is complementary in nucleotide sequence to at least part of the target RNA, and a catalytic region which is adapted to cleave the target RNA. The hybridizing region contains nine (9) or more nucleotides. Therefore, the hammerhead ribozymes of the present invention have a hybridizing region which is complementary to a gene encoding MTHFR and is at least nine nucleotides in length. The construction and production of such ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO 88/04300 by University Patents Inc.; Been and Cech, 1986, Cell, 47:207-216). The Cech endoribonucleases have an eight base pair active site which hybridizes to a target RNA sequence whereafter cleavage of the target RNA takes place.

There is a narrow range of binding free-energies between a ribozyme and its substrate that will produce maximal ribozyme activity. Such binding energy can be optimized by making ribozymes with G to I and U to BrU substitutions (or equivalent substitutions) in the substrate-binding arms. This allows manipulation of the binding free-energy without actually changing the target recognition sequence, the length of the two substrate-binding arms, or the enzymatic portion of the ribozyme. The shape of the free-energy vs. ribozyme activity curve can be readily determined using data from experiments in which each base (or several bases) is modified or unmodified, and without the complication of changing the size of the ribozyme/substrate interaction.

Such experiments will indicate the most active ribozyme structure. The use of modified bases thus permits "fine tuning" of the binding free energy to assure maximal ribozyme activity. In addition, replacement of such bases, e.g., I for G, may permit a higher level of substrate specificity when cleavage of non-target RNA is a problem.

The ability of the ribozymes of the present invention to inhibit MTHFR mRNA expression can be determined by a number of techniques known to one skilled in the art. For example, the level of MTHFR protein can be determined by standard Western blot analysis. Techniques of conducting this method are well-known to workers skilled in art (see, for example, Ausubel et al., (2000) *Current Protocols in Molecular Biology,* Wiley & Sons, New York: Coligan, et al., (2001) *Current Protocols in Protein Science,* Wiley & Sons, New York). In one embodiment of the present invention, the level of MTHFR protein is determined by measuring the level of MTHFR enzymatic activity, as described in Christensen, et al., (1997) *Arterioscler. Thromb. Vasc. Bio.,* 17:573-596. In an alternate embodiment, the level of MTHFR protein can be assessed by measuring the resulting increase in cellular levels of homocysteine, or decrease in 5-methyltetrahydrofolate or methionine, as described herein.

(iii) Biologically Inactive MTHFR Protein or Fragments of an MTHFR Protein

The present invention also contemplates the use of a biologically inactive MTHFR proteins or fragments of an MTHFR protein that interfere with the action of the wild-type protein and thus, acts as inhibitors of MTHFR activity.

Candidate inhibitory fragments can be selected from random fragments generated from the wild-type MTHFR protein. Methods for generating the candidate polypeptide fragments are well known to workers skilled in the art and include, but are not limited to, enzymatic, chemical or mechanical cleavage of the native protein, expression of nucleic acids encoding such fragments, etc. Biologically inactive MTHFR proteins can be generated by a variety of techniques known to a worker skilled in the art. For example, by site-directed or random mutagenesis techniques of nucleic acids encoding the protein, or by inactivation of the protein by chemical or physical means.

The ability of the biologically inactive MTHFR proteins or fragments to interfere with the wild-type MTHFR activity can be determined by standard techniques, for example, using the method described by Christensen, et al., (1997) *Arterioscler. Thromb. Vasc. Bio.*, 17:573-596, or competitive binding studies.

(iv) Peptide Inhibitors

The present invention also provides for polypeptides and peptides that bind to and inhibit the activity of the MTHFR protein. One exemplary method of identifying such peptides is by phage display techniques. Phage display libraries of random short peptides are commercially available, e.g. from New England Biolabs, Inc., and are utilized through an in vitro selection process known as "panning". In its simplest form, panning involves first incubating the library of phage displayed peptides with a plate, or bead, coated with the target molecule, then washing away unbound phage particles, and finally eluting the specifically bound phage. For the purposes of the present invention, the target molecule is the MTHFR protein, or a fragment thereof.

The peptide(s) displayed by the specifically-binding phage are then isolated and sequenced by standard techniques known to those skilled in the art. In some instances the binding strength of the isolated peptide is then tested using standard techniques. The ability of the peptides to inhibit MTHFR activity can also be determined using assays known in the art and as described herein.

(v) Small Molecule Inhibitors

Potential inhibitory compounds are screened from large libraries of synthetic or natural compounds. Numerous means are currently used for random and directed synthesis of saccharide, peptide, and nucleic acid based compounds and are well-known in the art. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are also available and can be prepared according to standard procedures. Alternatively, libraries of natural compounds in the form of bacterial, fungal, plant, and animal extracts are available from, e.g., Pan Laboratories (Bothell, Wash.) or MycoSearch (North Carolina), or are readily producible. Additionally, natural and synthetically produced libraries and compounds are readily modified through conventional chemical, physical, and biochemical means.

These libraries can be screened for their ability to inhibit the activity of the MTHFR protein (for example, using the method described by Christensen, et al., (1997) *Arterioscler. Thromb. Vasc. Bio.*, 17:573-596) or to inhibit expression of the MTHFR gene by techniques known in the art, e.g. nucleic acid binding assays, gel shift assays, and the like.

(vi) Antibodies

The present invention also contemplates the use of antibodies, and antibody fragments, raised against the MTHFR protein, or fragments thereof, as inhibitors of MTHFR activity.

For the production of antibodies, various hosts including goats, rabbits, rats, mice, humans, and others can be immunized by injection with the MTHFR protein, or with a fragment or oligopeptide thereof that has immunogenic properties. Depending on the host species, various adjuvants may be used to increase immunological response. Such adjuvants include, but are not limited to, Freund's adjuvant, mineral gels such as aluminum hydroxide, and surface active substances such as lysolecithin, pluronic polyols, polyanions, peptides, oil emulsions, Keyhole limpet hemolysin (KLH), and dinitrophenol. Examples of adjuvants used in humans include, BCG (bacilli Calmette-Guerin) and *Corynebacterium parvum*.

The oligopeptides, peptides, or fragments used to induce antibodies to MTHFR can have an amino acid sequence consisting of as little as about 5 amino acids. In one embodiment of the present invention, amino acid sequences of at least about 10 amino acids are used. These oligopeptides, peptides, or fragments can be identical to a portion of the amino acid sequence of the natural protein that contains the entire amino acid sequence of a small, naturally occurring molecule. If required, short stretches of MTHFR amino acids can be fused with those of another protein, such as KLH, and antibodies to the chimeric molecule can be produced.

Monoclonal antibodies to MTHFR can be prepared using techniques that provide for the production of antibody molecules by continuous cell lines in culture. These include, but are not limited to, the hybridoma technique, the human B-cell hybridoma technique, and the EBV-hybridoma technique (see, for example, Kohler, G. et al. (1975) *Nature* 256:495-497; Kozbor, D. et al. (1985) *J. Immunol. Methods* 81:31-42; Cote, R. J. et al. (1983) *Proc. Natl. Acad. Sci. USA*, 80:2026-2030; and Cole, S. P. et al. (1984) *Mol. Cell Biol.* 62:109-120). For example, the monoclonal antibodies according to the present invention can be obtained by immunizing animals, such as mice or rats, with purified MTHFR. Spleen cells isolated from the immunized animals are then immortalized using standard techniques. Those isolated immortalized cells whose culture supernatant contains an antibody that causes an inhibition of the activity of MTHFR with an $IC_{50}$ of less than 100 ng/ml are then selected and cloned using techniques that are familiar and known to one skilled in the art. The monoclonal antibodies produced by these clones are then isolated according to standard protocols.

The immortalization of the spleen cells of the immunized animals can be carried out by fusing these cells with a myeloma cell line, such as P3X63-Ag 8.653 (ATCC CRL 1580) according to the method in (1980) *J. Imm. Meth.* 39:285-308. Other methods known to a person skilled in the art can also be used to immortalize spleen cells. In order to detect immortalized cells that produce the desired antibody against the MTHFR protein, a sample of the culture supernatant is tested using an enzyme linked immunosorbent assay (ELISA) for reactivity with MTHFR. In order to obtain those antibodies that inhibit the enzymatic activity of MTHFR, the culture supernatant of clones that produce antibodies that bind to MTHFR is additionally examined for inhibition of MTHFR activity using an appropriate assay, such as those described herein. Those clones whose culture supernatant shows the desired inhibition of MTHFR activity are expanded and the antibodies produced by these clones are isolated according to known methods.

In addition, techniques developed for the production of "chimeric antibodies," such as the splicing of mouse antibody genes to human antibody genes to obtain a molecule with appropriate antigen specificity and biological activity, can be used (Morrison, S. L. et al. (1984) *Proc. Natl. Acad. Sci.* 81:6851-6855; Neuberger, M. S. et al. (1984) *Nature* 312:604-608; and Takeda, S. et al. (1985) *Nature* 314:452454). Alternatively, techniques described for the production of single chain antibodies can be adapted, using methods known in the art, to produce MTHFR-specific single chain antibodies. Antibodies with related specificity, but of distinct idiotypic composition, can be generated by chain shuffling from random combinatorial immunoglobulin libraries (see, for example, Burton D. R. (1991) *Proc. Natl. Acad. Sci. USA,* 88:10134-10137).

Antibodies can also be produced by inducing in vivo production in the lymphocyte population or by screening immunoglobulin libraries or panels of highly specific binding reagents as disclosed in the literature (Orlandi, R. et al. (1989) *Proc. Natl. Acad. Sci.* 86: 3833-3837; Winter, G. et al. (1991) *Nature* 349:293-299).

Antibody fragments which contain specific binding sites for MTHFR can also be generated. For example, such fragments include, but are not limited to, F(ab')2 fragments produced by pepsin digestion of the antibody molecule and Fab fragments generated by reducing the disulphide bridges of the F(ab')2 fragments. Alternatively, Fab expression libraries can be constructed to allow rapid and easy identification of monoclonal Fab fragments with the desired specificity (see, for example, Huse, W. D. et al. (1989) *Science,* 246:1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MTHFR and its specific antibody. Examples of such techniques include ELISAs, radioimmunoassays (RIAs), and fluorescence activated cell sorting (FACS). Alternatively, a two-site, monoclonal-based immunoassay utilizing monoclonal antibodies reactive to two non-interfering MTHFR epitopes, or a competitive binding assay can be used (see, Maddox, D. E. et al. (1983) *J. Exp. Med.* 158:1211-1216). These and other assays are well known in the art (see, for example, Hampton, R. et al. (1990) *Serological Methods: A Laboratory Manual*, APS Press, St Paul, Minn., Section IV; Coligan, J. E. et al. (1997, and periodic supplements) *Current Protocols in Immunology*, Wiley & Sons, New York, N.Y.; Maddox, D. E. et al. (1983) *J. Exp. Med.* 158:1211-1216).

Selection of MTHFR Inhibitors

In order for the inhibitors of the present invention to be effective, they must reduce the activity of MTHFR in cancer cells to an appropriate extent. As described above the extent of downregulation of MTHFR activity in response to an inhibitor can be measured in a number of ways. For example, by measuring the cellular level of mRNA or protein, by directly measuring the activity of the MTHFR protein, or by measuring increases in cellular homocysteine, or decreases in cellular 5-methyltetrahydrofolate or methionine, following treatment with a candidate inhibitor and comparing the results to those obtained in the absence of the candidate inhibitor.

Typically, an effective inhibitor will lower the level of MTHFR mRNA, protein, or enzymatic activity, or the level of 5-methyltetrahydrofolate or methionine in cells that have been administered with an MTHFR inhibitor by at least 20% when compared to the corresponding level in the absence of the inhibitor. More typically, the level will be lowered by at least 40%, frequently by at least 60%, by 80%, or by 90% and occasionally by at least 95%. When the level of cellular homocysteine is measured as an indicator of the effectiveness of the inhibitor, this level is typically at least 20% greater than in the absence of the inhibitor. More typically, the level will be increased by at least 40%, frequently by at least 60%, by 80%, or by 90%. The present invention also provides for inhibitors that result in levels of cellular homocysteine as much as 100%, 200% or even 500% greater than in the absence of the inhibitor.

Alternatively, the level of MTHFR mRNA, protein, or enzymatic activity in the presence of an inhibitor can be compared to the level in control cells that do not express functional MTHFR, such as cells homozygous for an MTHFR nonsense mutation. In this case, the level is typically equal to or less than 20-fold, more typically 5-fold and frequently 2-fold over the level in the control cell.

Testing the Effect of MTHFR Inhibitors on Cancer Cells

The ability of the inhibitors of the present invention to selectively inhibit the growth of cancer cells can be determined by treating a suitable cancer cell-line with the inhibitor and comparing the growth and/or survival of cells thus treated with an appropriate control. In order to determine the selectivity of the inhibitors, an untransformed cell-line can be treated with the inhibitor and monitored for growth and/or survival in a similar manner.

Examples of suitable cancer cell-lines for testing the effects of the MTHFR inhibitors of the present invention include, but are not limited to, colon carcinoma cell-lines SW40, LOVO, CaCo-2, Colo 320, SW620 and SW1222; neuroblastoma cell-lines BE(2)C and SK-N-F1; breast cancer cell-lines MCF7 and SKBr3; and glioma cell-line U87-lacZ. Many other appropriate cancer cell-lines are commercially available. Appropriate controls for these tests include untreated cells, cells treated with a control compound, such as a non-specific inhibitor, or untransformed cells treated with the inhibitor.

Typically, the percent of cancerous cells surviving the treatment is at least 20% lower than the initial number of cancerous cells, as measured using any standard assay, such as those described herein. More typically, the number is at least 40% lower, often at least 60% lower or 80% lower, and occasionally 100% lower. The MTHFR inhibitor of the present invention does not significantly affect non-cancerous cells that are not rapidly proliferating. In one embodiment of the present invention the ratio of percent survival of cancer cells over percent survival of normal cells, where the normal cells are not rapidly proliferating, is less than 1. More typically, this ratio is less than 0.9, 0.8, 0.7 or 0.6.

In accordance with the present invention, when the inhibitor is an antisense oligonucleotide, the number of cancerous cells present after administration of an MTHFR antisense nucleotide is at least 2-fold lower than the number of cancerous cells present after administration of a control oligonucleotide that has a polynucleotide sequence less than 70% identical to the reverse complement of a region of an MTHFR nucleic acid. More typically, the number is at least 5-fold greater, frequently at least 10-fold greater, 20-fold greater and occasionally 50-fold greater.

In one embodiment of the present invention, the effect of an antisense oligonucleotide inhibitor is determined by transfecting cancer cells with an inhibitor antisense oligonucleotide or a control oligonucleotide. The initial number of cells is determined, for example using a hemocytometer, and the number of cells surviving treatment is determined, for example using a colorimetric cell protein assay. The percentage of cells surviving the treatment can then be calculated. In a related embodiment, the specificity of the antisense oligonucleotide inhibitor in decreasing the growth of cancer cells only is measured by transfecting a fibroblast (i.e. untransformed) cell-line and determining cell survival as described above.

Administration of the MTHFR Inhibitors

The inhibitors of the present invention may be administered alone, or in the form of a pharmaceutical composition.

The present invention, therefore, provides pharmaceutical compositions comprising one or more MTHFR inhibitors and a pharmaceutically acceptable diluent or excipient. In the case of the pharmaceutical compositions that comprise an inhibitor according to the present invention that is an antisense oligonucleotide, the antisense oligonucleotide may be present as a vector encoding the antisense oligonucleotide. Similarly, in the case where the pharmaceutical composition comprises an inhibitor according to the present invention that is a proteinaceous molecule (i.e. an MTHFR fragment, an MTHFR mutant, an MTHFR specific antibody or a fragment thereof) the molecule may be present as a nucleic acid that encodes the molecule. In a related embodiment this nucleic acid is present in a vector.

The inhibitors of the present invention and pharmaceutical compositions comprising the inhibitors may be administered in a number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g. intrathecal or intraventricular, administration.

The inhibitors of the present invention may be delivered alone or in combination, and may be delivered along with a pharmaceutically acceptable vehicle. Ideally, such a vehicle would enhance the stability and/or delivery properties. The present invention also provides for administration of the inhibitors or pharmaceutical compositions comprising the inhibitors using a suitable vehicle, such as a liposome, microparticle or microcapsule. In various embodiments of the invention, the use of such vehicles may be beneficial in achieving sustained release of the active component.

For administration to an individual for the treatment of cancer, the present invention also contemplates the formulation of the inhibitors or pharmaceutical compositions comprising the inhibitors into oral dosage forms such as tablets, capsules and the like. For this purpose, the inhibitors or pharmaceutical compositions comprising the inhibitors can be combined with conventional carriers, such as magnesium carbonate, magnesium stearate, talc, sugar, lactose, pectin, dextrin, starch, gelatin, tragacanth, methylcellulose, sodium carboxymethyl-cellulose, low melting wax, cocoa butter and the like. Diluents, flavoring agents, solubilizers, lubricants, suspending agents, binders, tablet-disintegrating agents and the like can also be employed, if required. The inhibitors or pharmaceutical compositions comprising the inhibitors can be encapsulated with or without other carriers. In all cases, the proportion of active ingredients in any solid and liquid composition will be at least sufficient to impart the desired activity to the individual being treated upon oral administration. The present invention further contemplates parenteral injection of the inhibitors or pharmaceutical compositions comprising the inhibitors, in which case they are used in the form of a sterile solution containing other solutes, for example, enough saline or glucose to make the solution isotonic.

For administration by inhalation or insufflation, the inhibitors or pharmaceutical compositions comprising the inhibitors can be formulated into an aqueous or partially aqueous solution, which can then be utilized in the form of an aerosol. The present invention also contemplates topical use of the inhibitors or pharmaceutical compositions comprising the inhibitors. For this purpose they can be formulated as dusting powders, creams or lotions in pharmaceutically acceptable vehicles, which are applied to affected portions of the skin.

The present invention also provides for administration of antisense oligonucleotide, protein and peptide inhibitors in the form of a genetic vector construct that is designed to direct the in vivo synthesis of the inhibitor. Suitable vectors include viral vectors, such as an adenoviral, adeno-associated viral, retroviral, lentiviral, baculovirus, or herpes viral vectors. Within the vector construct, the nucleic acid sequence encoding the inhibitor is under the control of a suitable promoter. As described herein, the vector construct may additionally contain other regulatory control elements to provide efficient transcription and/or translation of the nucleic acid encoding the inhibitor.

The preparation of a vector comprising a nucleic acid sequence encoding and antisense oligonucleotide according to the present invention has been described herein. A worker skilled in the art would readily appreciate that a vector comprising the coding sequence for a proteinaceous inhibitor according to the present invention can be prepare using the same standard techniques.

Methods of constructing and administering such genetic vector constructs for the in vivo synthesis of antisense oligonucleotides, proteins or peptides are well-known in the art. For example, see Ausubel, et al., (2000) *Current Protocols in Molecular Biology*, Wiley & Sons, New York, N.Y. An efficient method for the introduction, expression and accumulation of antisense oligonucleotides in the cell nucleus is described in U.S. Pat. No. 6,265,167. This method allows the antisense oligonucleotide to hybridize to the sense mRNA in the nucleus, and thereby prevents the antisense oligonucleotide being either processed or transported into the cytoplasm.

The dosage requirements for the inhibitors of the present invention or pharmaceutical compositions comprising the inhibitors vary with the particular compositions employed, the route of administration, the severity of the symptoms presented and the particular subject being treated. Dosage requirements can be determined by standard clinical techniques known to a worker skilled in the art. Treatment will generally be initiated with small dosages less than the optimum dose of the compound. Thereafter the dosage is increased until the optimum effect under the circumstances is reached. In general, the inhibitors or pharmaceutical compositions comprising the inhibitors are administered at a concentration that will generally afford effective results without causing any harmful or deleterious side effects. Administration can be either as a single unit dose or, if desired, the dosage can be divided into convenient subunits that are administered at suitable times throughout the day.

Applications

The present invention provides MTHFR inhibitors that selectively decrease the growth of cancer cells, while leaving non-cancerous cells fully or partly unaffected. The inhibitors of the present invention, therefore, can be used to treat, stabilize or prevent cancer. In this context, the inhibitors exert cytotoxic or cytostatic effects that cause a reduction in the size of a tumor, slow or prevent an increase in the size of a tumor, increase the disease-free survival time between the disappearance of a tumor and its reappearance, prevent an initial or subsequent occurrence of a tumor (e.g. metastasis), or reduce an adverse symptom associated with a tumor.

The present invention also contemplates the use of the MTHFR inhibitors as "sensitizing agents," which selectively inhibit the growth of cancer cells. In this case, the inhibitor alone does not have a cytotoxic effect on the cell, but selectively arrests or slows the growth of cancer cells. The inhibitor thus provides a means of weakening the cancer cells, and thereby facilitates the benefit from conventional anti-cancer therapeutics.

In one embodiment of the present invention one or more MTHFR inhibitor is administered with one or more anti-cancer therapeutics. The one or more MTHFR inhibitor is administered before during or after treatment with the anti-cancer therapeutic. An "anti-cancer therapeutic" is any compound, composition or treatment that prevents or delays the growth and/or metastasis of cancer cells. Such anti-cancer therapeutics include but are not limited to chemotherapeutic drug treatment, radiation, gene therapy, hormonal manipulation, immunotherapy and antisense oligonucleotide therapy. It is to be understood that anticancer therapeutics for use in the present invention also include novel compounds or treatments developed in the future.

In accordance with the present invention the one or more MTHFR inhibitors or pharmaceutical compositions comprising the one or more MTHFR inhibitors is used to selectively inhibit cancer cells in vitro or in vivo, while leaving normal cells fully or partially unaffected. A further embodiment of the present invention provides a method for treating a mammal suffering from cancer by administering one or more MTHFR inhibitors or a pharmaceutical composition comprising one or more MTHFR inhibitors. In a related embodiment the MTHFR inhibitor or pharmaceutical compositions is used to selectively inhibit the growth and/or metastasis of cancer cells in vitro or in vivo in a mammal in need of such therapy. In a specific embodiment of the present invention the mammal is a human.

Examples of cancers that can be treated, stabilized, or prevented in accordance with the present invention include, but are not limited to, breast carcinomas, colon carcinomas, colorectal carcinomas, neuroblastomas, and gliomas. As used herein, "cancer" refers to all types of cancer or neoplasm or malignant tumors found in mammals, including carcinomas and sarcomas. Examples of cancers are cancer of the brain, breast, cervix, colon, head and neck, kidney, lung, non-small cell lung, melanoma, mesothelioma, ovary, sarcoma, stomach, uterus and Medulloblastoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas include chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriforn carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Kits

The present invention additionally provides for therapeutic kits containing the inhibitors in pharmaceutical compositions for use in the treatment of cancer. The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an infected area of the animal, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

To gain a better understanding of the invention described herein, the following examples are set forth. It should be understood that these examples are for illustrative purposes only. Therefore, they should not limit the scope of this invention in any way.

EXAMPLES

General
Cell Lines

Human fibroblasts MCH 51, MCH 75 and WG 1554 were obtained from the Repository for Mutant Human Cell Strains (Montreal Children's Hospital, Montreal, Canada). WG 1554 is homozygous for a nonsense mutation in MTHFR (Goyette et al, (1994) *Nature Genetics*, 7:175-200). Human colon carcinoma cell lines CaCo-2, Colo 320, and SW620 were obtained from American Type Culture Collection (Rockville Md.); human colon carcinoma cell line SW 1222 was a gift from Dr. N. Beauchemin (McGill University, Montreal, Canada). The carcinoma lines were genotyped for the MTHFR variant at bp 677 by PCR amplification and Hinfl digestion, as previously reported (Frosst et al, (1995) *Nature Genetics*, 10:111-113). SW 1222 and CaCo-2 were shown to carry the wild type alanine allele (A) whereas Colo 320 and SW620 carry the mutant valine allele (V). Two neuroblastoma lines, BE(2)C and SK-N-F1, were obtained from the American Type Culture Collection. The breast carcinoma cell lines, MCF7 and SKBr3, were a gift from Dr. Morag Park (McGill University, Montreal, Canada).

The MCF7 cell line was grown in α-MEM (Life Technologies, Rockville Md.) and the SKBr3 cell line was maintained in D-MEM (Life Technologies). Media for both lines was supplemented with 10% fetal bovine serum (Intergen, Purchase N.Y.). All other cell lines were grown in MEM (Life Technologies) supplemented with 5% fetal bovine serum (Intergen) and 5% iron enriched calf serum (Intergen).

All media was also supplemented with 50 IU/ml penicillin (Life Technologies), 50 µg/ml streptomycin (Life Technologies), 0.5 µg/ml fungizone reagent (Life Technologies). All cell lines were cultured in 75 cm$^2$ flasks in a humidified 37° C. incubator in 5% $CO_2$.

Deficient Culture Media

MEM and MEM without folate and methionine supplemented with 100 mM sodium pyruvate (F−M−) were obtained from Life Technologies. For methionine-deficient (M−) media, 2.3 µM folate (Sigma-Aldrich, Oakville ON) was added to the F−M− media. For all media, 5% fetal bovine serum (Intergen), 5% iron enriched calf serum (Intergen), 50 IU/ml penicillin (Life Technologies), 50 µg/ml streptomycin (Life Technologies), and 0.5 µg/ml fungizone reagent (Life Technologies) were added. For M−H+ media, 0.44 mM homocysteine (Sigma-Aldrich) and 1.5 µM vitamin $B_{12}$ (Sigma-Aldrich) was added to the M− media. Dialyzed serum was used for all deficient media.

Cell Survival Studies of Cells in Deficient Media

Cell viability studies were performed in 6-well tissue culture plates starting with 30,000-50,000 cells per well and 3 replicates for each condition. The initial number of cells were estimated with a hemacytometer. Cell survival in MEM was used as a control for proliferation in deficient media (M−, M−H+). Surviving cells were counted using the FluoroReporter Colorimetric Cell Protein Assay Kit (Molecular Probes, Eugene Oreg.).

Oligonucleotides

For assays to determine the effect of an MTHFR antisense oligonucleotide on cell viability, an antisense oligonucleotide, EX5, (phosphorothioate 5'-AGCTGCCGAAGG-GAGTGGTA-3') [SEQ ID NO:16] designed to bind exon 5 of MTHFR, a control oligonucleotide with six base pair mismatches, CT 677, (phosphorothioate 5'-TGCTGTCG-GAGCGATAGGTC-3') [SEQ ID NO:18], and a control oligonucleotide with a scrambled sequence, CTSEX5, (phosphorothioate 5'-GTGACGTAGGACAGCGATGG-3') [SEQ ID NO:17] were synthesized using standard solid-phase DNA synthesis procedures. This region of exon 5 was chosen because a BLAST search of the human expressed sequence (EST) database indicated that this sequence did not have significant identity to any other reported EST in humans. In addition, no sequence variations have been reported for this MTHFR exon, suggesting that an antisense oligonucleotide to exon 5 may bind all MTHFR alleles. The sequences of CT677 and CTSEX5 did not show homology to any known human genes in a BLAST search. These oligonucleotides were synthesized as phosphorothioate oligonucleotides in which one of the non-bridging phosphoryl oxygens of each nucleotide was replaced with sulphur. This modification dramatically improves nuclease stability and pharmacokinetics in vitro and in vivo.

Transfection with Oligonucleotides and Cell Counting

Cells were plated in 6-well dishes at 50-70% confluence and incubated overnight in complete medium (Life Technologies). Each well was washed once with OPTI-MEM I (Life Technologies). The cells were then overlayed with 1 ml of Opti-MEM I media containing 12 µg/ml Lipofectin reagent (Life Technologies) per 400 nM of oligonucleotide. The media was replaced with complete media (2-4 ml) after 5 hour incubation at 37° C. with the ASOs. Transfection with oligonucleotides was performed on 3 consecutive days followed by a 3-day period of regrowth in MEM. Cells were counted by SRB staining as outlined in the FluoroReporter Colorimetric Cell Protein Assay Kit (Molecular Probes). In each experiment, treatments were performed in triplicate.

In dose response experiments, the total oligonucleotide concentration was held constant at 400 nM by supplementing the tested oligonucleotide with the control oligonucleotide (Basilion et al, (1999) *Molec. Pharmacol.*, 56:359-369).

Protein Extraction after Treatment with Oligonucleotides

For Western blot analysis and MTHFR enzyme assays, $6\times10^5$ SW620 colon carcinoma cells were plated in 100 mm tissue culture treated petri dishes. After transfection of cells with oligonucleotides, the cells were harvested, and crude protein extracts from cell pellets were obtained by freezing the pellet at −70° C. and thawing to 4° C. three successive times. The cell pellet was then resuspended in 0.1 M $KPO_4$ pH 6.3 with 2 ug/ml aprotinin (Boehringer Mannheim, Laval, Quebec) and 2 ug/ml leupeptin (Amersham Pharmacia Biotech, Piscataway N.J.). Cellular debris was cleared by centrifugation at 14,000 rpm for 10 min. Protein concentration was assayed using the Bradford method (Bradford, 1976) according to the manufacturer's instructions (BioRad, Mississauga ON).

MTHFR Enzyme Assay

Enzyme activity was measured in the reverse direction, in crude protein extracts, as previously described (Christensen et al, (1997) *ARTERIOSCLER. Thromb. Vasc. Biol.*, 17:569-573). Equal amounts of protein (~60 µg) were used per assay. Enzyme activity was expressed as nmol formaldehyde formed per mg protein/h.

Western Blot Analysis

Equal amounts of protein (35-60 µg) were loaded onto a 10% SDS polyacrylamide gel. Transfer was performed in a transfer buffer (39 mM glycine, 49 mM Tris base, 0.037% SDS, 20% methanol) for 2-3 hour at 70 V to nitrocellulose (Hybond ECL membrane, Amersham Pharmacia Biotech). The membrane was blocked with 5% non-fat skim milk in PBS-0.5% Tween 20 (Tween 20; BioRad) overnight at 4° C. The MTHFR protein was detected using a rabbit anti-porcine MTHFR antibody at a dilution of 1:1000 in 5% non-fat skim milk in PBS-0.5% Tween 20 incubated for 4 to 6 hour at 4° C. After three successive washes in PBS-0.5% Tween 20, anti-rabbit horseradish peroxidase-conjugated antibody (Amersham Pharmacia Biotech) was used as a secondary antibody. The immunocomplexes were visualized by enhanced chemiluminescence with an ECL kit (Amersham Pharmacia Biotech). Quantitation of protein was determined by scanning the films with a flat-bed scanner (Hewlett Packard Scan). The MTHFR and actin band areas were calculated; MTHFR protein level is expressed as a ratio of MTHFR/actin.

Statistical Analysis

One-way ANOVA was performed using SPSS software, Version 10.0 (SPSS Inc., Chicago Ill.), to analyze cell survival after treatment with EX5. The Student t-test was used to evaluate differences in MTHFR activity, and to analyze cell survival data of fibroblast cell lines treated with EX5 antisense.

Example 1

Decreased Cell Viability in Cancer Cells after Transfection of an MTHFR Antisense Oligonucleotide The following cancer cell lines were used in these experiments: SW620 colon carcinoma (ATCC Accession No. CCL-227), LOVO colon carcinoma (ATCC Accession No. CCL 229), BEC 2 neuroblastoma (ATCC Accession No. CRL 2268), SK-N-F1 neuroblastoma (ATCC Accession No. CRL 2142), MCF7 breast cancer (ATCC Accession No. HTB 2), SKBr3 breast cancer (ATCC Accession No. HTB 30), and U87-lacZ glioma cell lines (Li et al., (1999) *Clin. Cancer Res.* 5:637-642).

Prior to the transfection of tumor cells with these phosphorothioate oligonucleotides, the cells were plated at 50-60% confluence in 6-well plates or 10 cm tissue culture dishes and incubated overnight at 37° C. and 5% $CO_2$. The next day, the cells were washed with OPTI-MEM I Reduced Serum Media (Gibco, BRL) and treated with the indicated concentration of the MTHR antisense oligonucleotide or one of the control oligonucleotides (FIGS. 3-11) and 12 ug/ml Lipofectin Reagent (Gibco-BRL) in OPTI-MEM I Reduced Serum Media. For the U87-lacZ glioma cell line, the control oligonucleotide CT677 was used as the control oligonucleotide; for all the other cell lines, the scrambled oligonucleotide CTSEX5 was used as the control oligonucleotide.

After a five hour incubation at 37° C. and 5% $CO_2$ to allow transfection of the oligonucleotide into the cells, the OPTI-MEM I Reduced Serum Media containing the oligonucleotide and Lipofectin was replaced with MEM supplemented with 5% FBS and 5% calf serum. The next day the transfection protocol was repeated. For the second transfection, the cells were washed with Opti-MEM I media and incubated for five hours with the MTHFR antisense or control oligonucleotide and Lipofectin reagent, as described above. Then, the media was replaced with MEM supplemented with 5% FBS and 5% calf serum. The following day, a third transfection was performed as described for the second transfection. After this transfection, the cells were allowed to grow in the supplemented MEM media for two to four days. Then, the number of cells attached to the tissue culture dish was determined using a colorimetric cell protein assay kit, according to the manufacturer's protocol (FluoroReporter® Colorimetric Cell Protein Assay Kit F-2961 from Molecular Probes, Eugene Oreg.). This kit contains the anionic xanthene dye, sulforhadamine B, that forms an electrostatically stabilized complex with basic amino acid residues under moderately acidic conditions. This protein-dye complex was detected spectrophotometrically after removal of unbound die from TCA-fixed cells.

Example 2

Figure 10:
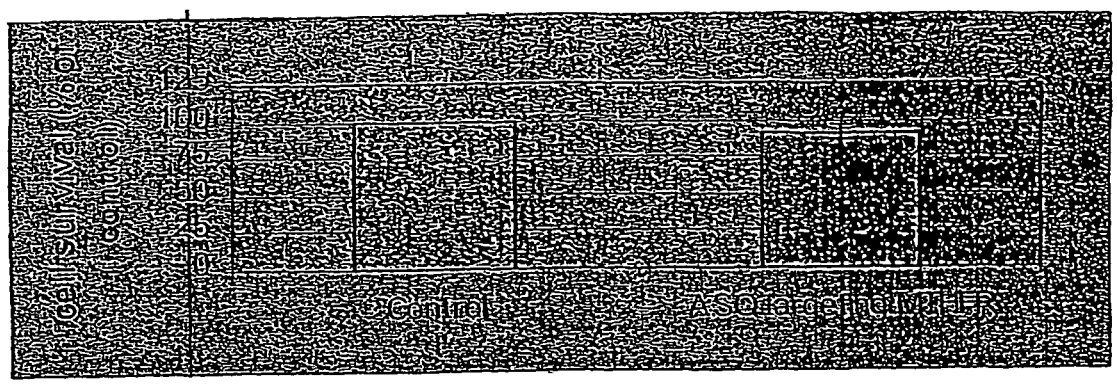
FIG. 10 demonstrates the percent survival of WG1554 fibroblast cells homozygous for a nonsense mutation in MTHFR which were treated with 400 nM MTHFR antisense or control oligonucleotide and allowed to recover for three days, as described for FIG. 3.
Figure 11:
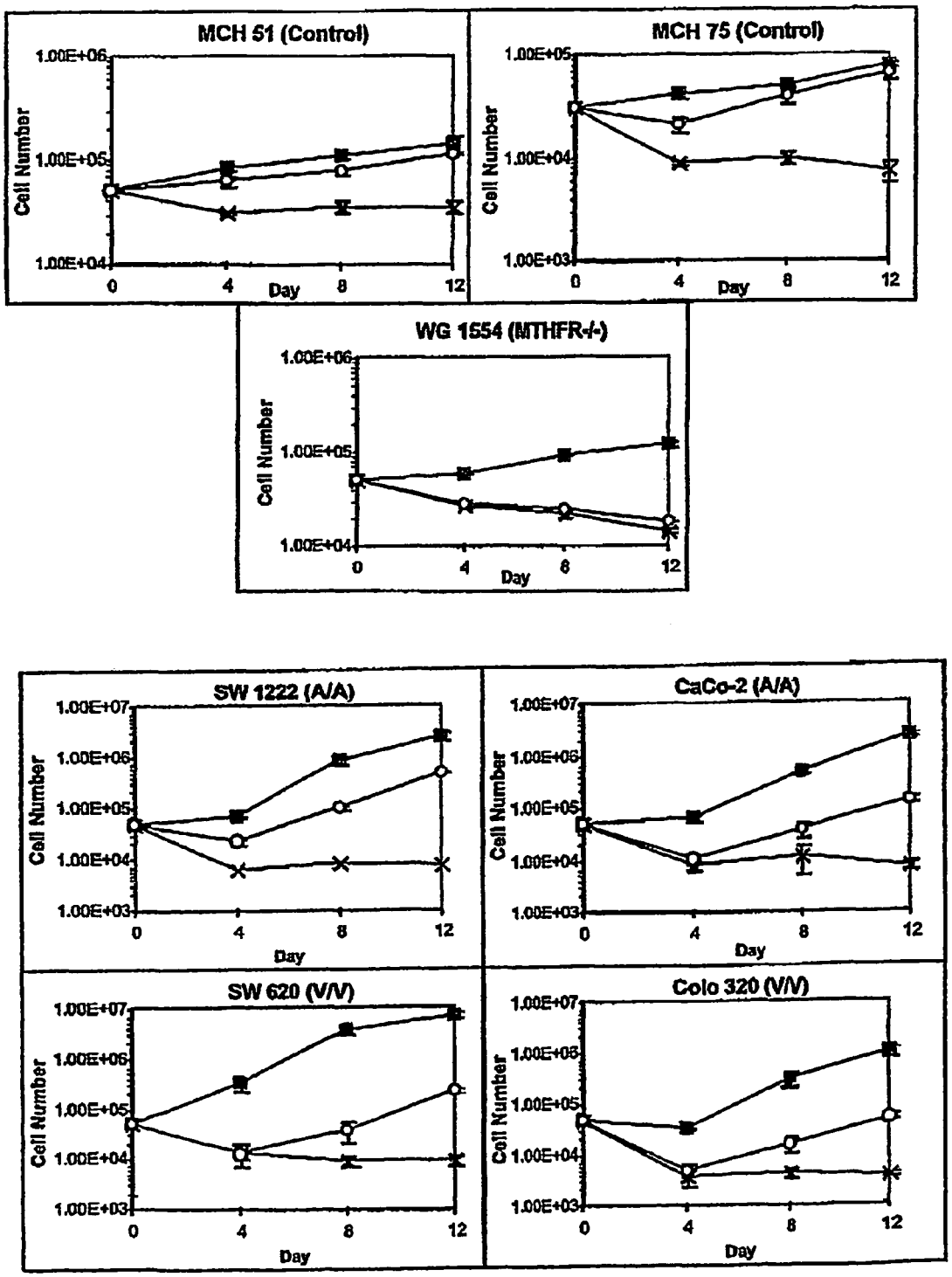
FIG. 11 depicts the growth of fibroblast cell lines in deficient media. Two wild type fibroblast cell lines (MCH 51, MCH 75) and an MTHFR null mutant (WG 1554) were grown in MEM (■), M– (×), and M–H+ (μ) for 12 days. The number of cells for each line was counted using the SRB assay at 3 time points. Each point represents the mean of 3 replicates ±SD.

Failure of an MTHFR Antisense Oligonucleotide to Reduce Cell Viability of Non-cancerous Cells To determine the effect of an MTHFR antisense oligonucleotide on non-cancerous cells, the human diploid fibroblast cell line WG 1554, which carries 2 nonsense mutations for MTHFR and thus does not produce functional MTHFR protein, was also tested in the above transfection assay (Goyette et al., (1994) *Nat. Genet.* 7:195-200). In particular, the cells were subjected to three rounds of transfection with 400 nM of the antisense oligonucleotide designed to bind exon 5 of MTHFR or the control oligonucleotide and allowed to recover for three days. In contrast to the previous results with tumor cell lines, there was no difference in cell survival between WG1554 cells treated with the MTHFR antisense or control oligonucleotide (FIG. 10). This result indicates that the MTHFR antisense oligonucleotide is more toxic to cancerous cells than non-cancerous cells that do not express MTHFR. Thus, MTHFR antisense oligonucleotides may produce few adverse side-effects if administered to human subjects.

Example 3

MTHFR Antisense Oligonucleotides Decrease the Cell Viability of Methionine-dependent Transformed Cells Three fibroblast strains (FIG. 11) and 4 colon carcinoma lines (FIG. 12) were grown in MEM, MEM without methionine (M−), or MEM without methionine supplemented with homocysteine and vitamin $B_{12}$ (M−H+). The latter medium served to examine de novo synthesis of methionine from homocysteine and 5-methyltetrahydrofolate, catalyzed by vitamin $B_{12}$-dependent methionine synthase. 5-Methyltetrahydrofolate is the product of the MTHFR reaction. All seven lines showed sensitivity to the M− medium; growth was significantly reduced in this medium compared to that in MEM. Control fibroblasts (MCH 51, MCH 75) could maintain virtually normal growth in the M−H+ medium. However, the fibroblast strain WG 1554, which is homozygous for a nonsense mutation in MTHFR (Goyette et al, 1994), was unable to restore growth in the M−H+ medium. The carcinoma lines cultured in the M−H+ medium increased their proliferation only slightly through endogenous methionine synthesis (FIG. 12). The cell numbers were just a small percentage (5%-20%) of the values obtained in MEM. These carcinoma lines are not compromised with respect to MTHFR activity, although two of the lines (Colo 320 and SW620) have the valine allele, which is associated with mild enzymatic deficiency.

FIG. 13A demonstrates a dose-dependent decrease in cell survival ($p<0.01$, one-way ANOVA) after treatment of SW620 carcinoma cells with the MTHFR antisense oligonucleotide EX5. At the maximal dose of 400 nM, cell survival decreased approximately 80% compared to that of cells treated with the scrambled control oligonucleotide CTSEX5.

To ensure that MTHFR expression was altered, Western blotting was used to analyze immunoreactive MTHFR protein, after three consecutive treatments with the EX5 ASO. FIG. 13B demonstrates a significant decrease in MTHFR protein levels after EX5 treatment, compared to treatment with the scrambled control, CTSEX5, or compared to treatment with Lipofectin reagent only (mock transfection). After normalization to actin, MTHFR protein levels following treatment with the control oligo were 94% of mock-treated cells, whereas treatment with 200 nM and 400 nM of EX5, MTHFR protein levels were 39% and 25%, respectively, of that in mock-treated cells (average of 3 Western blots).

Example 4

Cell Survival of Normal Human Fibroblasts, Breast Carcinoma Cells and Neuroblastoma Lines after Treatment with 400 nM of EX5

Figure 14:
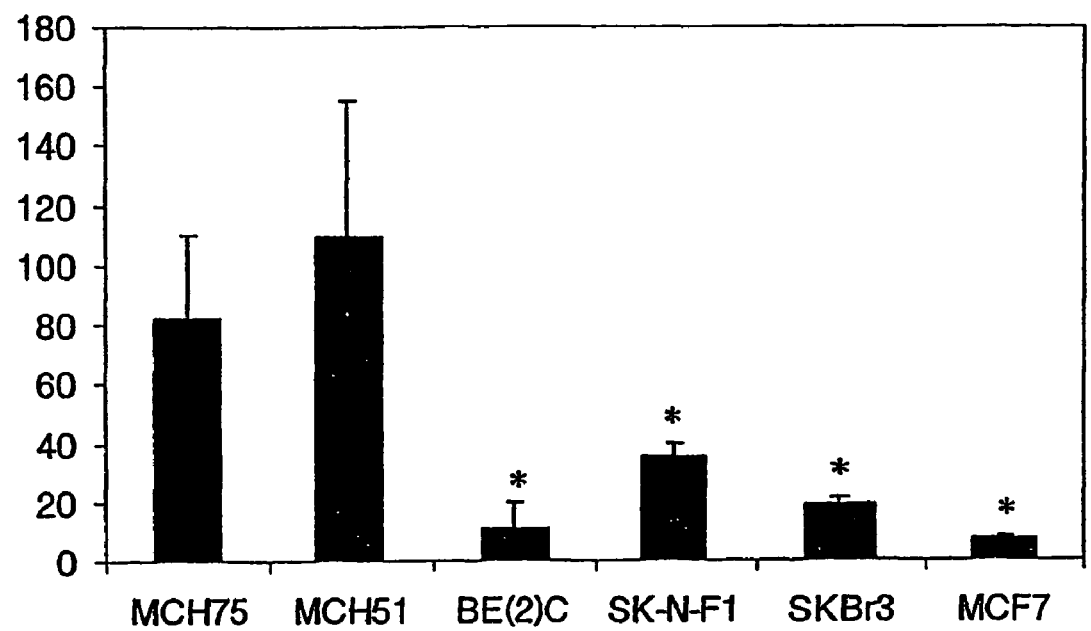
FIG. 14 depicts a comparison of the cell survival of normal human fibroblasts, breast carcinoma cells and neuroblastoma lines after treatment with 400 nM of EX5. Cells were treated three successive days with 400 nM of EX5 and 400 nM of CTSEX5. The number of surviving cells was determined by SRB staining as described in Materials and Methods. For each cell line, cell survival after transfection with EX5 is expressed as a % of survival after transfection with the control CTSEX5 oligonucleotide. Each value on the graph represents the mean of three replicates ±SD.

After treatment with 400 nM of EX5 as described above, two neuroblastoma cell lines (BE(2)C and SK-N-F1) showed significant decreases in cell survival compared to control ASO treated cells: decreases of 80% ($p<0.001$) and 65% ($p<0.01$), respectively. Similarly, the breast carcinoma cell line SKBr3 showed a 80% ($p<0.0001$) decrease in cell survival and the MCF7 breast carcinoma line showed a 92% ($p<0.0001$) reduction in cell survival compared to control oligonucleotide CTSEX5 treated cells. Contrary to data obtained in transformed lines, two normal human fibroblast cell lines (MCH 75 and MCH 51) treated with 400 nM of EX5 did not exhibit significant differences in cell survival compared to CTSEX5 treated cells ($p>0.05$). These results are summarized in FIG. 14.

Example 5

In vivo Effects of the Downregulation of MTHFR Expression on Tumours

The Min (multiple intestinal neoplasia) mouse is an established mouse model for colon cancer. It carries a mutation in the APC gene, the same gene that is mutated in human hereditary and sporadic colorectal tumours. These mice develop multiple tumors (from 30 to 100) at several months of age.

Min mice, which carry one copy of the APC mutation, were crossed to MTHFR-deficient mice with a heterozygous knockout of the MTHFR gene. These heterozygous mice carry one copy of the null allele (Mthfr +/−) and, therefore, have 50% of MTHFR activity compared to normal mice.

Min mice (n=20) carrying just the APC mutation had a mean tumor number of 75±6.6 (standard error), whereas the Min mice with the APC mutation as well as a MTHFR null allele had a mean tumor number of 36±2.7. This difference in tumor number is highly significant ($p<0.0001$). In addition, the sizes of the tumors were smaller in the Min mice carrying the MTHFR mutation (91.9% of tumors were less than 1 mm), compared to Min mice without the MTHFR mutation (76.3% of tumors were less than 1 mm).

Therefore, partial inhibition of MTHFR in transformed cells is associated with decreased numbers of tumors and decreased tumor growth. Partial inhibition of MTHFR in normal cells does not appear to be deleterious, since the mice with a heterozygous knockout of MTHFR (Mthfr +/−), without any other mutations, are similar to the normal mice in appearance, birth weight, growth and survival.

These studies suggest that inhibition of MTHFR may be more deleterious to rapidly-growing cells than to normal cells. This is consistent with studies in cultured cells outlined above, which demonstrate that transformed cells have a higher requirement for methionine than normal cells.

Example 6

In Vivo Animal Model for Study of MTHFR Antisense Oligonucleotides

For in vivo testing of MTHFR inhibitors, the previously described nude mouse cancer model may be used (Bufalo et al., (1996) *British J. Canc.* 74:387-393; Dean et al., (1996) *Cancer Res.* 56:3499-3507; Hasegawa et al., (1998) Int. J. Cancer 76:812-816; Narayanan, (1994) In Vivo 8: 787-794). Briefly, cancer cells are injected subcutaneously into the flank of a nu/nu athymic mouse. The size of the resulting tumor is measured regularly. When the tumor volume reaches 100 mm$^3$-200 mm$^3$, an MTHFR inhibitor or control compound is injected subcutaneously at the site of the tumor. For initial experiments, a dose of 200:g inhibitor is injected every other day for a period of one to two weeks. During this period, the appearance and size of the tumor is monitored. After the series of injections is completed, the mouse is sacrificed, and the tumor is removed for further analysis.

After the efficacy of subcutaneous administration of the inhibitor has been determined, intravenous injections may be performed to evaluate the efficacy of various doses and dosing frequencies for systemic administration of the inhibitor. This information may be used to determine the appropriate dosing schedule for human clinical trials. If desired, MTHFR inhibitors may also be tested in other standard animal models for cancer, such as naturally-occurring or induced cancers in other mammals including rats, dogs, or monkeys.

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. An inhibitor of methylenetetrahydrofolate reductase (MTHFR) that selectively inhibits cancer cell growth in a mammal comprising an antisense oligonucleotide of 20 to about 50 nucleotides in length that is at least 90% identical to the complement of a region of exon 5 of a human MTHFR mRNA and comprises the sequence as set forth in SEQ ID NO: 16, wherein said human MTHFR mRNA has the sequence as set forth in SEQ ID NO: 1.

2. A nucleic acid sequence encoding the inhibitor according to claim 1.

3. The nucleic acid sequence according to claim 2, which is operatively associated with a regulatory control element.

4. A vector comprising the nucleic acid sequence according to claim 2 operatively associated with a regulatory control element.

5. A composition comprising the inhibitor according to claim 1 and a pharmaceutically acceptable carrier, diluent or excipient.

6. A method of preparing a medicament comprising admixing the inhibitor according to claim 1 with a pharmaceutically acceptable carrier, wherein the inhibitor reduces or inhibits MTHFR gene expression.

7. The inhibitor according to claim 1, wherein said antisense oligonucleotide comprises a sequence that is about 20 to about 22 nucleotides in length.

8. The inhibitor according to claim 1, wherein said antisense oligonucleotide is a phosphorothioate oligonucleotide.

9. The inhibitor according to claim 1, wherein said antisense oligonucleotide comprises a sequence that is at least 95% identical to the complement of a region of exon 5 of the human MTHFR mRNA.

10. The inhibitor according to claim 1, wherein said antisense oligonucleotide comprises a sequence that is identical to the complement of a region of exon 5 of the human MTHFR mRNA.

11. The inhibitor according to claim 1, wherein said antisense oligonucleotide is a modified oligonucleotide.

12. The inhibitor according to claim 11, wherein said modified oligonucleotide is nuclease resistant, has improved pharmacokinetics relative to an unmodified oligonucleotide, or a combination thereof.

13. An inhibitor of methylenetetrahydrofolate reductase (MTHFR) that selectively inhibits cancer cell growth in a mammal comprising an antisense oligonucleotide of 20 to about 25 nucleotides in length that is at least 90% identical to the complement of a region of exon 5 of a human MTHFR mRNA and comprises the sequence as set forth in SEQ ID NO: 16, wherein said human MTHFR has the sequence as set forth in SEQ ID NO: 1.

14. The inhibitor according to claim 13, wherein said antisense oligonucleotide is at least 95% identical to the complement of a region of exon 5 of the human MTHFR mRNA.

15. The inhibitor according to claim 13, wherein said antisense oligonucleotide is identical to the complement of a region of exon 5 of a human MTHFR mRNA.

16. The inhibitor according to claim 13, wherein said antisense oligonucleotide comprises a sequence that is about 20 to about 22 nucleotides in length.

17. The inhibitor according to claim 13, wherein said antisense oligonucleotide is a modified oligonucleotide.

18. The inhibitor according to claim 17, wherein said modified oligonucleotide is nuclease resistant, has improved pharmacokinetics relative to an unmodified oligonucleotide, or a combination thereof.

19. The inhibitor according to claim 13, wherein said antisense oligonucleotide is a phosphorothioate oligonucleotide.

20. A composition comprising the inhibitor according to claim 13 and a pharmaceutically acceptable carrier, diluent or excipient.

21. An inhibitor of methylenetetrahydrofolate reductase (MTHFR) that selectively inhibits cancer cell growth in a mammal comprising an antisense oligonucleotide of 20 to about 50 nucleotides in length that is complementary to a region of exon 5 of a human MTHFR mRNA and comprises the sequence as set forth in SEQ ID NO: 16, wherein said human MTHFR mRNA has the sequence as set forth in SEQ ID NO: 1, and wherein said antisense oligonucleotide is a modified oligonucleotide.

22. The inhibitor according to claim 21, wherein said modified oligonucleotide is nuclease resistant, has improved pharmacokinetics relative to an unmodified oligonucleotide, or a combination thereof.

23. The inhibitor according to claim 21, wherein said antisense oligonucleotide is about 20 to about 25 nucleotides in length.

24. The inhibitor according to claim 21, wherein said antisense oligonucleotide is about 20 to about 22 nucleotides in length.

25. The inhibitor according to claim 21, wherein said antisense oligonucleotide is a phosphorothioate oligonucleotide.

26. A composition comprising the inhibitor according to claim 21 and a pharmaceutically acceptable carrier, diluent or excipient.

27. A vector comprising a nucleic acid encoding the inhibitor according to claim 13 operatively associated with a regulatory control element.

28. A composition comprising the vector according to claim 4 and a pharmaceutically acceptable carrier, diluent or excipient.

29. A composition comprising the vector according to claim 27 and a pharmaceutically acceptable carrier, diluent or excipient.

30. The inhibitor according to claim 1, wherein said antisense oligonucleotide is a DNA oligonucleotide.

31. The inhibitor according to claim 1, wherein said antisense oligonucleotide is a RNA oligonucleotide.

32. The inhibitor according to claim 13, wherein said antisense oligonucleotide is a DNA oligonucleotide.

33. The inhibitor according to claim 13, wherein said antisense oligonucleotide is a RNA oligonucleotide.

34. The inhibitor according to claim 21, wherein said antisense oligonucleotide is a DNA oligonucleotide.

35. The inhibitor according to claim 21, wherein said antisense oligonucleotide is a RNA oligonucleotide.

* * * * *

SEQUENCE LISTING

<160> NUMBER OF SEQ ID NOS: 16

<210> SEQ ID NO 1
<211> LENGTH: 2219
<212> TYPE: DNA
<213> ORGANISM: Homo sapiens

<400> SEQUENCE: 1

```
aattccggag ccatggtgaa cgaagccaga ggaaacagca gcctcaaccc ctgcttggag      60
ggcagtgcca gcagtggcag tgagagctcc aaagatagtt cgagatgttc caccccgggc     120
ctggaccctg agcggcatga gagactccgg gagaagatga ggcggcgatt ggaatctggt     180
gacaagtggt tctccctgga attcttccct cctcgaactg ctgagggagc tgtcaatctc     240
atctcaaggt ttgaccggat ggcagcaggt ggcccctct acatagacgt gacctggcac     300
ccagcaggtg accctggctc agacaaggag acctcctcca tgatgatcgc cagcaccgcc     360
gtgaactact gtggcctgga gaccatcctg cacatgacct gctgccgtca gcgcctggag     420
gagatcacgg gccatctgca caaagctaag cagctgggcc tgaagaacat catggcgctg     480
cggggagacc caataggtga ccagtgggaa gaggaggagg aggcttcaa ctacgcagtg     540 gacctggtga agcacatccg aagtgagttt ggtgactact ttgacatctg tgtggcaggt     600 tacccaaag gccaccccga agcagggagc tttgaggctg acctgaagca cttgaaggag     660
aaggtgtctg cgggagccga tttcatcatc acgcagcttt tcttgaggc tgacacattc     720 ttccgctttg tgaaggcatg caccgacatg ggcatcactt gccccatcgt ccccgggatc     780
tttcccatcc agggctacca ctcccttcgg cagcttgtga agctgtccaa gctggaggtg     840
ccacaggaga tcaaggacgt gattgagcca atcaaagaca acgatgctgc catccgcaac     900
tatggcatcg agctggccgt gagcctgtgc caggagcttc tggccagtgg cttggtgcca     960
ggcctccact tctacacccct caaccgcgag atggctacca cagaggtgct gaagcgcctg    1020
gggatgtgga ctgaggaccc caggcgtccc ctaccctggg ctctcagtgc ccacccaag    1080 cgccgagagg aagatgtacg tcccatcttc tgggcctcca gaccaaagag ttacatctac    1140
cgtacccagg agtgggacga gttccctaac ggccgctggg gcaattcctc ttcccctgcc    1200
```

-continued

```
tttggggagc tgaaggacta ctacctcttc tacctgaaga gcaagtcccc caaggaggag       1260
ctgctgaaga tgtgggggga ggagctgacc agtgaagcaa gtgtctttga agtctttgtt       1320
ctttacctct cgggagaacc aaaccggaat ggtcacaaag tgacttgcct gccctggaac       1380
gatgagcccc tggcggctga gaccagcctg ctgaaggagg agctgctgcg ggtgaaccgc       1440
cagggcatcc tcaccatcaa ctcacagccc aacatcaacg ggaagccgtc ctccgacccc       1500
atcgtgggct ggggccccag cggggctat gtcttccaga aggcctactt agagttttc       1560 acttcccgcg agacagcgga agcacttctg caagtgctga gaagtacga gctccgggtt       1620 aattaccacc ttgtcaatgt gaagggtgaa acatcacca atgcccctga actgcagccg       1680
aatgctgtca cttggggcat cttccctggg cgagagatca tccagcccac cgtagtggat       1740
cccgtcagct tcatgttctg gaaggacgag gcctttgccc tgtggattga gcggtgggga       1800
aagctgtatg aggaggagtc cccgtcccgc accatcatcc agtacatcca cgacaactac       1860
ttcctggtca acctggtgga caatgacttc ccactggaca actgcctctg gcaggtggtg       1920
gaagacacat tggagcttct caacaggccc acccagaatg cgagagaaac ggaggctcca       1980
tgaccctgcg tcctgacgcc ctgcgttgga gccactcctg tcccgccttc ctcctccaca       2040
gtgctgcttc tcttgggaac tccactctcc ttcgtgtctc tcccaccccg gcctccactc       2100
ccccacctga caatggcagc tagactggag tgaggcttcc aggctcttcc tggacctgag       2160
tcggccccac atgggaacct agtactctct gctctaaaaa aaaaaaaaa aaaggaatt       2219
```

```
<210> SEQ ID NO 2
<211> LENGTH: 656
<212> TYPE: PRT
<213> ORGANISM: Homo sapiens

<400> SEQUENCE: 2
```

```
Met Val Asn Glu Ala Arg Gly Asn Ser Ser Leu Asn Pro Cys Leu Glu
 1               5                  10                  15

Gly Ser Ala Ser Ser Gly Ser Glu Ser Ser Lys Asp Ser Ser Arg Cys
            20                  25                  30

Ser Thr Pro Gly Leu Asp Pro Glu Arg His Glu Arg Leu Arg Glu Lys
        35                  40                  45

Met Arg Arg Arg Leu Glu Ser Gly Asp Lys Trp Phe Ser Leu Glu Phe
    50                  55                  60

Phe Pro Pro Arg Thr Ala Glu Gly Ala Val Asn Leu Ile Ser Arg Phe
65                  70                  75                  80

Asp Arg Met Ala Ala Gly Gly Pro Leu Tyr Ile Asp Val Thr Trp His
                85                  90                  95

Pro Ala Gly Asp Pro Gly Ser Asp Lys Glu Thr Ser Ser Met Met Ile
            100                 105                 110

Ala Ser Thr Ala Val Asn Tyr Cys Gly Leu Glu Thr Ile Leu His Met
        115                 120                 125

Thr Cys Cys Arg Gln Arg Leu Glu Glu Ile Thr Gly His Leu His Lys
    130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Gly Gly Phe Asn Tyr Ala Val
                165                 170                 175

Asp Leu Val Lys His Ile Arg Ser Glu Phe Gly Asp Tyr Phe Asp Ile
            180                 185                 190

Cys Val Ala Gly Tyr Pro Lys Gly His Pro Glu Ala Gly Ser Phe Glu
```

-continued

```
            195                 200                 205
Ala Asp Leu Lys His Leu Lys Glu Lys Val Ser Ala Gly Ala Asp Phe
210                 215                 220
Ile Ile Thr Gln Leu Phe Phe Glu Ala Asp Thr Phe Arg Phe Val
225                 230                 235                 240
Lys Ala Cys Thr Asp Met Gly Ile Thr Cys Pro Ile Val Pro Gly Ile
                245                 250                 255
Phe Pro Ile Gln Gly Tyr His Ser Leu Arg Gln Leu Val Lys Leu Ser
                260                 265                 270
Lys Leu Glu Val Pro Gln Glu Ile Lys Asp Val Ile Glu Pro Ile Lys
                275                 280                 285
Asp Asn Asp Ala Ala Ile Arg Asn Tyr Gly Ile Glu Leu Ala Val Ser
290                 295                 300
Leu Cys Gln Glu Leu Leu Ala Ser Gly Leu Val Pro Gly Leu His Phe
305                 310                 315                 320
Tyr Thr Leu Asn Arg Glu Met Ala Thr Thr Glu Val Leu Lys Arg Leu
                325                 330                 335
Gly Met Trp Thr Glu Asp Pro Arg Arg Pro Leu Pro Trp Ala Leu Ser
                340                 345                 350
Ala His Pro Lys Arg Glu Glu Asp Val Arg Pro Ile Phe Trp Ala
                355                 360                 365
Ser Arg Pro Lys Ser Tyr Ile Tyr Arg Thr Gln Glu Trp Asp Glu Phe
                370                 375                 380
Pro Asn Gly Arg Trp Gly Asn Ser Ser Pro Ala Phe Gly Glu Leu
385                 390                 395                 400
Lys Asp Tyr Tyr Leu Phe Tyr Leu Lys Ser Lys Ser Pro Lys Glu Glu
                405                 410                 415
Leu Leu Lys Met Trp Gly Glu Glu Leu Thr Ser Glu Ala Ser Val Phe
                420                 425                 430
Glu Val Phe Val Leu Tyr Leu Ser Gly Glu Pro Asn Arg Asn Gly His
                435                 440                 445
Lys Val Thr Cys Leu Pro Trp Asn Asp Glu Pro Leu Ala Ala Glu Thr
                450                 455                 460
Ser Leu Leu Lys Glu Glu Leu Leu Arg Val Asn Arg Gln Gly Ile Leu
465                 470                 475                 480
Thr Ile Asn Ser Gln Pro Asn Ile Asn Gly Lys Pro Ser Ser Asp Pro
                485                 490                 495
Ile Val Gly Trp Gly Pro Ser Gly Gly Tyr Val Phe Gln Lys Ala Tyr
                500                 505                 510
Leu Glu Phe Phe Thr Ser Arg Glu Thr Ala Glu Ala Leu Leu Gln Val
                515                 520                 525
Leu Lys Lys Tyr Glu Leu Arg Val Asn Tyr His Leu Val Asn Val Lys
                530                 535                 540
Gly Glu Asn Ile Thr Asn Ala Pro Glu Leu Gln Pro Asn Ala Val Thr
545                 550                 555                 560
Trp Gly Ile Phe Pro Gly Arg Glu Ile Ile Gln Pro Thr Val Val Asp
                565                 570                 575
Pro Val Ser Phe Met Phe Trp Lys Asp Glu Ala Phe Ala Leu Trp Ile
                580                 585                 590
Glu Arg Trp Gly Lys Leu Tyr Glu Glu Glu Ser Pro Ser Arg Thr Ile
                595                 600                 605
Ile Gln Tyr Ile His Asp Asn Tyr Phe Leu Val Asn Leu Val Asp Asn
610                 615                 620
```

```
Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
            645                 650                 655
```

<210> SEQ ID NO 3
<211> LENGTH: 346
<212> TYPE: DNA
<213> ORGANISM: Homo sapiens
<220> FEATURE:
<221> NAME/KEY: misc_feature
<222> LOCATION: (326)...(328)
<223> OTHER INFORMATION: n= a, t, g or c

<400> SEQUENCE: 3

```
gggtgtggct gcctgccccc tgatgctccc tgccccaccc tgtgcagtag gaacccagcc      60
atggtgaacg aagccagagg aaacagcagc ctcaacccct gcttggaggg cagtgccagc     120
agtggcagtg agagctccaa agatagttcg agatgttcca ccccgggcct ggaccctgag     180
cggcatgaga gactccggga gaagatgagg cggcgattgg aatctggtga caagtggttc     240
tccctggaat tcttccctcc tcgaactgct gagggagctg tcaatctcat ctcaaggtaa     300
actcatgcaa ggttaaggtg ggaggnnnga gtggtggtgc ctgggg                    346
```

<210> SEQ ID NO 4
<211> LENGTH: 339
<212> TYPE: DNA
<213> ORGANISM: Homo sapiens

<400> SEQUENCE: 4

```
acggatggta tttctcctgg aacctctctt cagaaacaaa ccccctacag gtttgaccgg      60
atggcagcag gtggcccect ctacatagac gtgacctggc acccagcagg tgaccctggc     120
tcagacaagg agacctcctc catgatgatc gccagcaccg ccgtgaacta ctgtggcctg     180
gagaccatcc tgcacatgac ctgctgccgt cagcgcctgg aggagatcac gggccatctg     240
cacaaagcta agcagctggg cctgaagaac atcatggcgc tgcggggagg tgtggagcca     300
gcactcccct acactctggg ttctggcttt cccggaggc                            339
```

<210> SEQ ID NO 5
<211> LENGTH: 210
<212> TYPE: DNA
<213> ORGANISM: Homo sapiens

<400> SEQUENCE: 5

```
tctggaggtt gggtgagacc cagtgactat gacctccacc aaccctgcag acccaatagg      60
tgaccagtgg gaagaggagg agggaggctt caactacgca gtggacctgg tgaagcacat     120
ccgaagtgag tttggtgact actttgacat ctgtgtggca ggtgagtggc tggatcatcc     180
tggtggcggg gatggagcta gggaggctga                                      210
```

<210> SEQ ID NO 6
<211> LENGTH: 294
<212> TYPE: DNA
<213> ORGANISM: Homo sapiens
<220> FEATURE:
<221> NAME/KEY: misc_feature
<222> LOCATION: (260)
<223> OTHER INFORMATION: n = a, t, g or c

<400> SEQUENCE: 6

```
ccttgaacag gtggaggcca gcctctcctg actgtcatcc ctattggcag gttaccccaa        60
aggccacccc gaagcaggga gctttgaggc tgacctgaag cacttgaagg agaaggtgtc       120
tgcgggagcc gatttcatca tcacgcagct tttctttgag gctgacacat tcttccgctt       180
tgtgaaggca tgcaccgaca tgggcatcac ttgccccatc gtccccggga tctttcccat       240
ccaggtgagg ggcccaggan agcccataag ctccctccac cccactctca ccgc             294
```

```
<210> SEQ ID NO 7
<211> LENGTH: 341
<212> TYPE: DNA
<213> ORGANISM: Homo sapiens

<400> SEQUENCE: 7
gctggccagc agccgccaca gcccctcatg tcttggacag gctaccact cccttcggca        60 gcttgtgaag ctgtccaagc tggaggtgcc acaggagatc aaggacgtga ttgagccaat      120
caaagacaac gatgctgcca tccgcaacta tggcatcgag ctggccgtga gcctgtgcca      180
ggagcttctg gccagtggct tggtgccagg cctccacttc tacaccctca accgcgagat     240
ggctaccaca gaggtgctga gcgcctggg gatgtggact gaggacccca ggtgagggca      300
gtggcccaga gatccccaga ggagggtcca agagcagccc c                          341
```

```
<210> SEQ ID NO 8
<211> LENGTH: 235
<212> TYPE: DNA
<213> ORGANISM: Homo sapiens

<400> SEQUENCE: 8
tccctctagc caatcccttg tctcaattct ctgtccccat cctcacccag gcgtccccta       60
ccctgggctc tcagtgccca ccccaagcgc cgagaggaag atgtacgtcc catcttctgg     120
gcctccagac caaagagtta catctaccgt acccaggagt gggacgagtt ccctaacggc     180
cgctggtgag ggcctgcaga ccttccttgc aaatacatct ttgttcttgg gagcg           235
```

```
<210> SEQ ID NO 9
<211> LENGTH: 281
<212> TYPE: DNA
<213> ORGANISM: Homo sapiens

<400> SEQUENCE: 9
actgccctct gtcaggagtg tgccctgacc tctgggcacc cctctgccag gggcaattcc       60
tcttcccctg cctttgggga gctgaaggac tactacctct tctacctgaa gagcaagtcc     120
cccaaggagg agctgctgaa gatgtggggg gaggagctga ccagtgaagc aagtgtcttt     180
gaagtctttg ttctttacct ctcgggagaa ccaaaccgga tggtcacaa agtgagtgat      240 gctggaagtg gggaccctgg ttcatcccct gcccctggcc t                          281
```

```
<210> SEQ ID NO 10
<211> LENGTH: 283
<212> TYPE: DNA
<213> ORGANISM: Homo sapiens

<400> SEQUENCE: 10
cagggtgcca aacctgatgg tcgcccagc cagctcaccg tctctcccag gtgacttgcc        60
tgccctggaa cgatgagccc ctggcggctg agaccagcct gctgaaggag gagctgctgc     120
gggtgaaccg ccagggcatc ctcaccatca actcacagcc caacatcaac gggaagccgt     180
cctccgaccc catcgtgggc tggggcccca gcggggggcta tgtcttccag aaggtgtggt     240
```

-continued

```
agggaggcac ggggtgcccc cctctcttga ccggcacccg tgg           283

<210> SEQ ID NO 11
<211> LENGTH: 202
<212> TYPE: DNA
<213> ORGANISM: Homo sapiens
<220> FEATURE:
<221> NAME/KEY: misc_feature
<222> LOCATION: (187)
<223> OTHER INFORMATION: n = a, t, g or c
<220> FEATURE:
<221> NAME/KEY: misc_feature
<222> LOCATION: (195)
<223> OTHER INFORMATION: n = a, t, g or c

<400> SEQUENCE: 11
gggcgtctgg cagggctggg gttggtgaca ggcacctgtc tctcccacag gcctacttag     60
agtttttcac ttcccgcgag acagcggaag cacttctgca agtgctgaag aagtacgagc    120
tccgggttaa ttaccacctt gtcaatgtga aggtaggcca ggccccacgg ttcccacaga    180
gtaccangcc cttcnttgaa ca                                             202

<210> SEQ ID NO 12
<211> LENGTH: 220
<212> TYPE: DNA
<213> ORGANISM: Homo sapiens

<400> SEQUENCE: 12
actccagttg ttcttggccc aggtcttacc cccaccccac atccctcag ggtgaaaaca      60 tcaccaatgc ccctgaactg cagccgaatg ctgtcacttg gggcatcttc cctgggcgag    120
agatcatcca gcccaccgta gtggatcccg tcagcttcat gttctggaag gtaaaggagc    180
gggggcaagc ttgccccgcc cacctggaaa accgtgggga                          220

<210> SEQ ID NO 13
<211> LENGTH: 522
<212> TYPE: DNA
<213> ORGANISM: Homo sapiens
<220> FEATURE:
<221> NAME/KEY: misc_feature
<222> LOCATION: (512)
<223> OTHER INFORMATION: n = a, t, g or c
<220> FEATURE:
<221> NAME/KEY: misc_feature
<222> LOCATION: (520)
<223> OTHER INFORMATION: n = a, t, g or c

<400> SEQUENCE: 13
ctctgtgtgt gtgtgcatgt gtgcgtgtgt gcggggtat gtgtgtgtag gacgaggcct      60
ttgccctgtg gattgagcgg tggggaaagc tgtatgagga ggagtccccg tcccgcacca    120
tcatccagta catccacgac aactacttcc tggtcaacct ggtggacaat gacttcccac    180
tggacaactg cctctggcag gtggtggaag acacattgga gcttctcaac aggcccaccc    240
agaatgcgag agaaacggag gctccatgac cctgcgtcct gacgcccgtc gttggagcca    300
ctcctgtccc gccttcctcc tccacagtgc tgcttctctt gggaactcca ctctccttcg    360
tgtctctccc accccggcct ccactccccc acctgacaat ggcagctaga ctggagtgag    420
gcttccaggc tcttcctgga cctgagtcgg ccccacatgg gaacctagta ctctctgctc    480
tagccaggag tctgtgctct tttggtgggg ancacttgcn tc                       522

<210> SEQ ID NO 14
```

-continued

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
agctgccgaa gggagtggta                                                    20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gtgacgtagg acagcgatgg                                                    20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
tgctgtcgga gcgataggtc                                                    20
```